United States Patent
Weiss

(10) Patent No.: US 6,581,445 B1
(45) Date of Patent: Jun. 24, 2003

(54) DISTRIBUTED FIBER OPTIC MOISTURE INTRUSION SENSING SYSTEM

(75) Inventor: Jonathan D. Weiss, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 48 days.

(21) Appl. No.: 09/608,334

(22) Filed: Jun. 29, 2000

(51) Int. Cl.[7] .......................... G01N 5/02; G01N 25/00
(52) U.S. Cl. ................................ 73/75; 73/73
(58) Field of Search .................... 174/115; 340/604; 73/73, 75, 768, 866.5, 29.01, 29.02, 29.03, 29.04, 29.05

(56) References Cited

U.S. PATENT DOCUMENTS

| | | | | |
|---|---|---|---|---|
| 5,005,005 A | * | 4/1991 | Brossia et al. | 340/604 |
| 5,111,525 A | * | 5/1992 | Hartouni | 385/126 |
| 5,287,734 A | * | 2/1994 | Cuming | 73/75 |
| 5,696,863 A | * | 12/1997 | Kleinerman | 385/123 |
| 5,892,176 A | * | 4/1999 | Findlay et al. | 174/115 |
| 6,167,525 A | * | 12/2000 | Donazzi et al. | 713/330 |

OTHER PUBLICATIONS

Technical Aspects of Optical Fibre Distributed Temperature Sensing, York Sensors Ltd.
J. P. Dakin, *Chapter 15—Distributed Optical Fiber Sensor Systems*, Optical Fiber Sensors: Systems and Applications, edited by Brian Culshaw & John Dakin, vol. Two, Artech House, 1989 Pp. 575–587.
Distributed Temperature Sensing—DTS 800 Brochure by York Power Industry.

* cited by examiner

*Primary Examiner*—Helen Kwok
*Assistant Examiner*—Rodney Frank
(74) *Attorney, Agent, or Firm*—Russell D. Elliott

(57) ABSTRACT

Method and system for monitoring and identifying moisture intrusion in soil such as is contained in landfills housing radioactive and/or hazardous waste. The invention utilizes the principle that moist or wet soil has a higher thermal conductance than dry soil. The invention employs optical time delay reflectometry in connection with a distributed temperature sensing system together with heating means in order to identify discrete areas within a volume of soil wherein temperature is lower. According to the invention an optical element and, optionally, a heating element may be included in a cable or other similar structure and arranged in a serpentine fashion within a volume of soil to achieve efficient temperature detection across a large area or three dimensional volume of soil. Remediation, moisture countermeasures, or other responsive action may then be coordinated based on the assumption that cooler regions within a soil volume may signal moisture intrusion where those regions are located.

15 Claims, 31 Drawing Sheets

DISTRIBUTED FIBER OPTIC MOISTURE INTRUSION SENSING SYSTEM

This invention was made with support from the United States Government under Contract DE-AC04-96AL85000 awarded by the U.S. Department of Energy. The Government has certain rights in this invention.

BACKGROUND OF THE INVENTION

1. Field of the Invention

This invention pertains generally to moisture detection in soil, and more specifically to a method and apparatus using principles of thermal conductance to detect intrusion of moisture into soil and landfills containing toxic and/or radioactive waste.

2. Description of the Related Art

Thousands of landfills exist across the U.S. which are operated by both government and private entities. Many such landfills contain chemical waste, low-level radioactive waste and/or mixed waste. Moisture intrusion into the soil comprising such landfills represents a problem in that wastes can be destabilized or even mobilized resulting in inadequate containment. Moisture, from precipitation (rain and snow, for example), or from overland runoff can mobilize waste resulting in contamination of ground water sources thereby creating a health hazard. Therefore, effective and economical monitoring of the presence and movement of moisture in landfills is often critical to environmental safety and remediation programs.

Various containment methods including using barrier covers, liners and in-situ grouting have been proposed and used in many government and private remediation sites. Additionally, though, long term (10's of years) and short term (0 to 5 years) monitoring is required to address concerns of stakeholders as well as to satisfy regulatory requirements. Fundamental to many containment approaches is the need for a clear understanding of how fluids move through, accumulate in, and leave soils (or subsurface wastes and containment structures).

A need remains, therefore, for a reliable sensor system that can detect in situ the intrusion of moisture in soil wherein hazardous and/or radioactive waste is stored. The present invention aids in this understanding by providing a method and apparatus for monitoring fluid flow in situ.

SUMMARY OF THE INVENTION

It is an object of the present invention to provide a sensing system and method that detects moisture intrusion in soil using a simple apparatus operating in situ in soil containing wastes of concern.

It is another object of the present invention to provide a sensing system and method that infers the presence of moisture based on temperature differences detectable using a distributed temperature sensing element.

It is yet another object of the invention to rely on different thermal conductances of dry soil, slightly moist soil and saturated soil to detect presence and location of moisture in soil.

It is yet another object of the invention to utilize application of heat to soil in order to isolate where regions having different thermal conductances are located in a volume of soil being investigated (sometimes referred to as the "target area" in this disclosure).

Yet another object is to provide a soil moisture sensing system that includes a linear element (such as a tube, cable or conduit) positioned in a volume of soil. Another related object is the provision of a distributed temperature sensing element associated with the linear element that permits identification of the regions having different thermal conductances mentioned above, especially when a heater is included, which, when actuated, heats the soil.

Yet another object of the invention is to provide a method for detecting moisture intrusion in soil which includes positioning in soil a linear element that comprises a distributed temperature sensing element, and further includes heating at least a portion of the soil, and measuring temperatures in the soil. Using the invention in this way, it is possible to ascertain whether regions are present in the soil suggesting different thermal conductances and, therefore, possibly the presence of moisture.

These and other objects are fulfilled and satisfied by the claimed invention which utilizes a linear element such as a cable, tube or conduit positioned in a serpentine fashion within a target area of soil. Optimal placement of the linear element assumes that it passes through a significant two-dimensional area and, preferably, also a significant three-dimensional volume within the target portion of the soil. The invention also includes using an optical fiber, that forms a component of a distributed temperature sensing system, and a heating element. The optical fiber serves as an optical conduit through which pulses of light pass, generating Raman scattered radiation within the target area. The scattered radiation is detected and analyzed using principles of optical time delay reflectometry (OTDR) to permit accurate and distributed temperature detection capability along the length of the fiber optic. The heating element which, in a primary embodiment disclosed here, is integrated with the cable or other linear element, is used to heat soil. Principles of the invention, though, would also be served using by an external heating apparatus. The heating causes regions of differing thermal conductance within the soil to become apparent and detectable by the distributed temperature detection system. According to the invention, those areas having relatively higher thermal conductance (possibly reflecting the presence of moisture) can thus be identified and located.

Additional advantages and novel features will become apparent to those skilled in the art upon examination of the following description or may be learned by practice of the invention. The objects and advantages of the invention may be realized and attained by means of the instrumentalities and combinations particularly pointed out in the appended claims.

DESCRIPTION OF THE FIGURES

The accompanying drawings, which are incorporated into and form part of the specification, illustrate embodiments of the invention and, together with the description, serve to explain the principles of the invention.

DETAILED DESCRIPTION OF THE INVENTION

Figure 1:
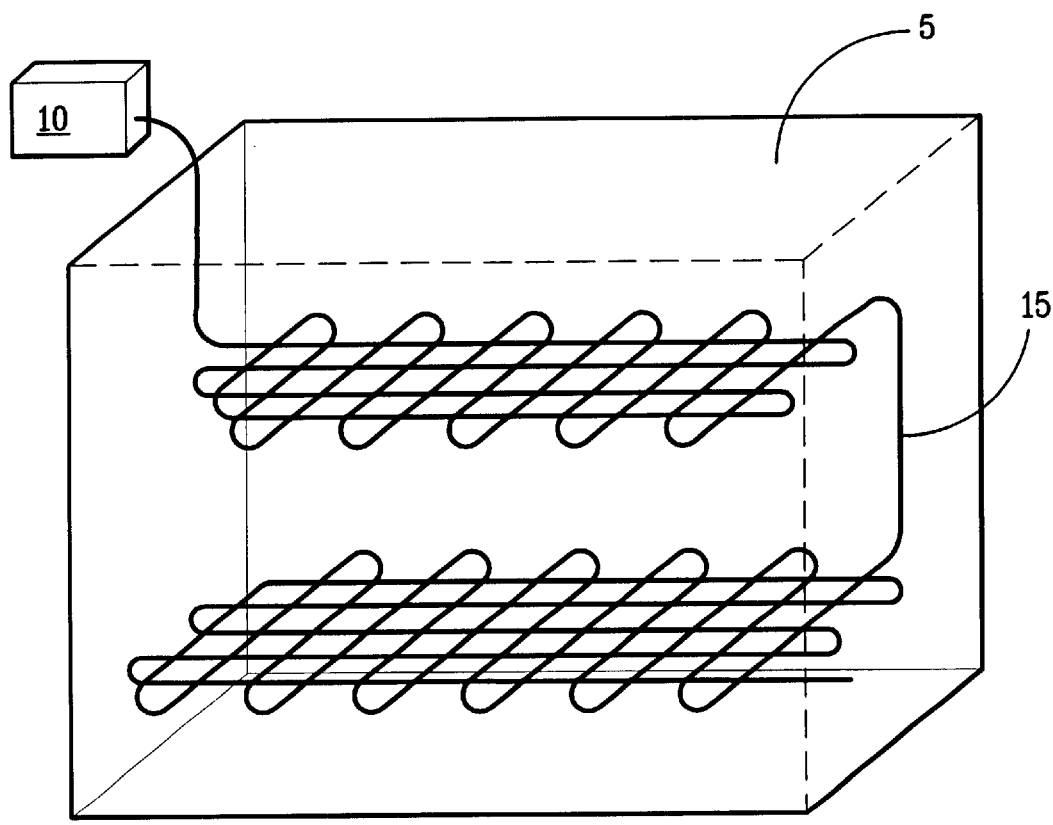
FIG. 1 is a schematic perspective view of one embodiment of the invention illustrating positioning, within soil of a landfill, of a linear element including a distributed temperature sensing element.

Reliable and inexpensive detection of moisture intrusion, for example, in a landfill, is obtained using the present invention which involves heating soil slightly, and then monitoring temperatures at various points within the soil to identify regions exhibiting a relative decrease in temperature where moisture has penetrated the soil. This drop will often be quite dramatic because the thermal conductance of saturated, or near saturated, sand, for example, is so much greater than that of dry sand, where dead air spaces exist between the grains.

High resolution detection of differences in thermal conductance is possible through the present invention by its employment of OTDR principles, known to those skilled in the art of distributed temperature measurement. Novelty and nonobviousness of the present invention resides in part in the application of DTS (distributed temperature sensing) principles in combination with means for creating conditions within a volume of soil wherein discernment of differences in thermal conductance across a target area is made optimally possible.

Distributed temperature measurement in the invention is accomplished using a system such as can be purchased by York Sensors Limited, York House, Premier Way, Abbey Park, Hampshire SO51 9AQ, UK. With such a system, temperature resolution of about 1C and a spatial resolution of about ½ meter can be obtained, which can be suitable for purposes of the monitoring objectives identified at the outset of this disclosure. Fundamentally, the temperature sensing component works by sending pulses of radiation down a fiber optic (at 1064 nm, in the case of the York system), in OTDR-like fashion, generating Raman scattered radiation throughout. The latter consists of two components, one with a wavelength slightly above 1064 nm and the other slightly below 1064 nm.

It is noted the 1064 nm reference is simply an example. York uses it, but use of that specific wavelength is not a necessity. Other wavelengths could also be used. The wavelength shift involved is well understood by those skilled in the art of OTDR, however, in a general sense, the York sensor utilizes both the "Stokes" component of the scattered radiation (having a wavelength slightly longer than 1064 nm) and the "antiStokes" component (having a wavelength slightly shorter than 1064 nm). These components are shifted by about ±50 nm, respectively, from the 1064 nm. This is the shift that can be observed when using communications grade optical fiber; other materials exhibit different shifts.

The intensity of the two components of the radiation varies with temperature. Hence, the ratio of the anti-Stokes component to the Stokes component depends on temperature. For the optical fiber mentioned, the ratio of anti-Stokes to Stokes is $K \exp(-700/T)$, at the point of generation, where T is the absolute temperature and K is a coefficient that depends on the numerical aperture of the fiber and wavelengths raised to the fourth power.

Of course, differences in transmission loss between the two components from the point of generation to the detector have to be taken into account for an accurate temperature measurement. This may be done by means of a "double ended" configuration, by which means scattered radiation moving both forward and backward through the fiber optic is detected at each scattered wavelength. In addition, the time between detected signals and the launching of the initial pulse must be known in order to determine where calculational necessities are built into the system (such as the York system). What is then automatically displayed using the commercial system is a temperature profile along the fiber.

In the present invention, a distributed temperature sensing apparatus such as that just described is integrated with a cable, conduit or other similar linear element that can be positioned according to a serpentine arrangement in a target area within a volume of soil. (It is noted that, for purposes of this disclosure, the phrase "target area" includes not only a two-dimensional geometric area but also a three-dimensional volume.) The linear element may be flexible or rigid, depending on a particular application or user's needs.

One embodiment of the described linear element can include a cable that houses both the optical fiber as well as a heater wire. Other configurations, though, are possible and considered within the scope of the invention and appended claims. Such other configurations include, but are not limited to, arrangements such as those employing a conduit in place of a conventional cable, and configurations wherein the heater wire is omitted, and another form of heater is used in its place. Alternative embodiments also include, for example, deploying a stainless steel tube housing the optical fiber as the heating element. This is described in slightly more detail, below. Also, as mentioned earlier, the heater need not necessarily even be integrated with the linear element, so long as the desired separation in temperature between moist and dry soil can be attained.

FIG. 1 is a schematic illustration of the various elements just described showing pictorially an embodiment of the invention. Referring to the figure, a three-dimensional landfill volume 5 is shown. Also shown is a data acquisition and processing system 10 such as would be employed in connection with a commercially-sold DTS system. The data acquisition and processing system is shown in the figure as being outside of the landfill volume being monitored (e.g. at the surface), however, its location is of little consequence to effective operation of the invention. Finally, the figure shows a cable 15, which could, for example, contain the optical fiber element described as well as a heating wire. One end of the cable is in operative association with the data acquisition and processing system 10. In the illustrated embodiment, the remainder of the cable is arranged within the landfill volume 5 in a serpentine fashion. Shown is one possible cable deployment suited to detect moisture intrusion at two levels within the landfill. Additional levels could obviously be added. Likewise, other placements of the cable within a volume of soil would be suitable for given circumstances. While they are generally considered to be within the scope of the appended claims, it is recognized that a variety of other placement configurations of a cable or other linear element containing the fiber optic are possible. It is anticipated that users of the invention will adapt the invention in this aspect to suit their particular needs without departing from the spirit and scope of the appended claims.

EXAMPLES

Figure 2A:
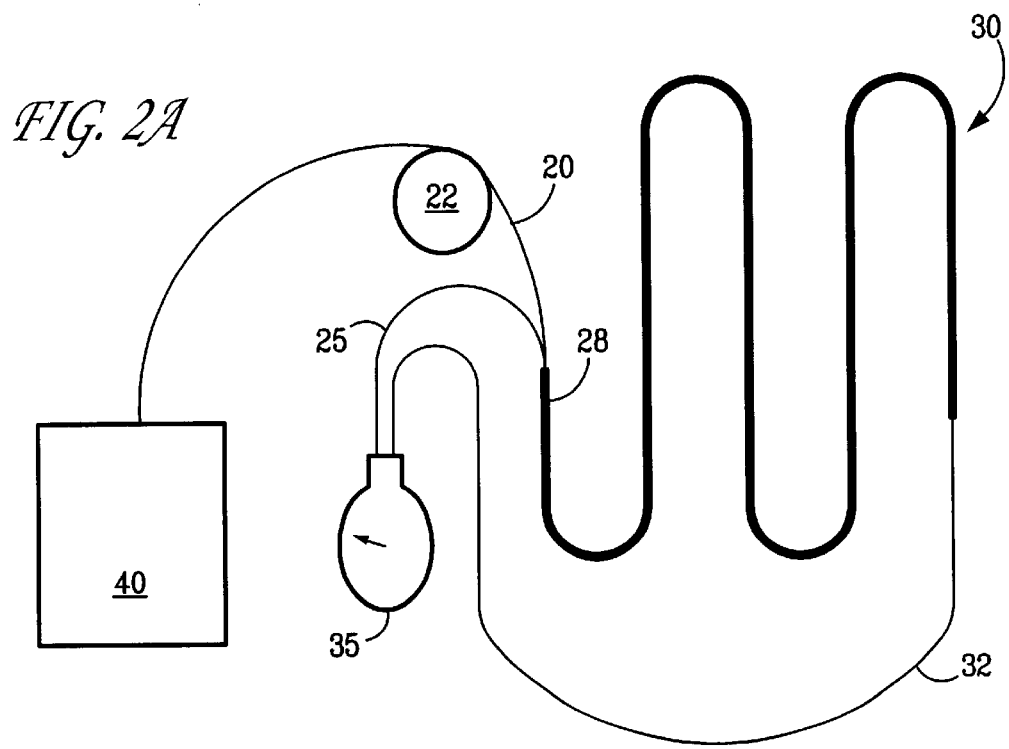
FIG. 2a is a schematic depiction of various aspects of the invention according to one embodiment, those aspects including a cable that houses heating and sensing elements.

The following describes various tests that have been performed which demonstrate the basic operating principles of the invention as well as the effectiveness of several different embodiments. FIG. 2a illustrates schematically the experimental arrangement used in demonstrating operation of the invention. Approximately 14 meters of fiber 20 at the end of a long spool 22 and heater wire 25 were fed through shrink tubing 28 forming a cable and then laid out in a serpentine pattern 30 on a surface. Certain additional necessary components needed for the heater and DTS system to be operative are also shown in the figure. Those include an electrical lead 32 connecting the heater wire to an electric potential, in this case, provided by a variac 35. The optical fiber 20 is likewise in operative association with a commercial DTS data acquisition and processing unit 40 which is capable of displaying temperature values measured at various locations along the length of the cable, according to the ODTR and DTS principles discussed above.

Each FIGS. 3–26 illustrate graphs depicting temperature readings in degrees Celsius along various positions identified according to their distance (in meters) along the length of the cable. In one set of measurements, (shown in FIGS. 3–6), no sand was used, and towels saturated with tap water were applied to sections of the cable during various stages of heating. The next set of measurements (depicted in FIGS. 7–9) pertain to tests where sand was used to at least partially cover the cable. The temperature distribution along the cable was measured using the DTS.

Figure 3:
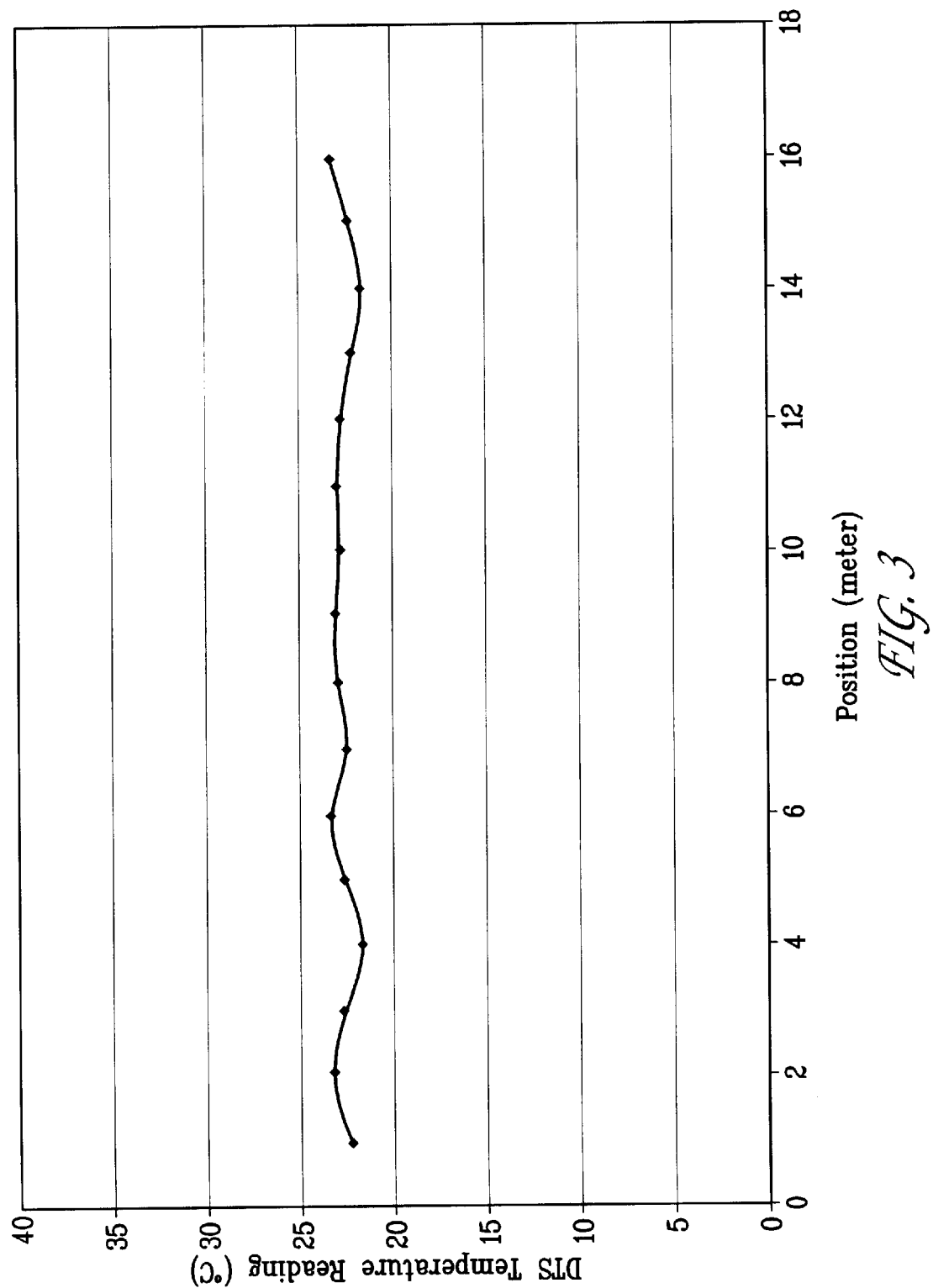
FIGS. 3–26 and 28–31 are graphs showing temperature data illustrating the efficacy of the invention principles according to various apparatus configurations and under a variety of conditions.

FIG. 3 is a plot of results of a baseline test showing temperature variations along the fiber absent heating or localized cooling. Only mild variations in temperature are registered, and those are considered to be within expected degree of random variation.

Figure 4:
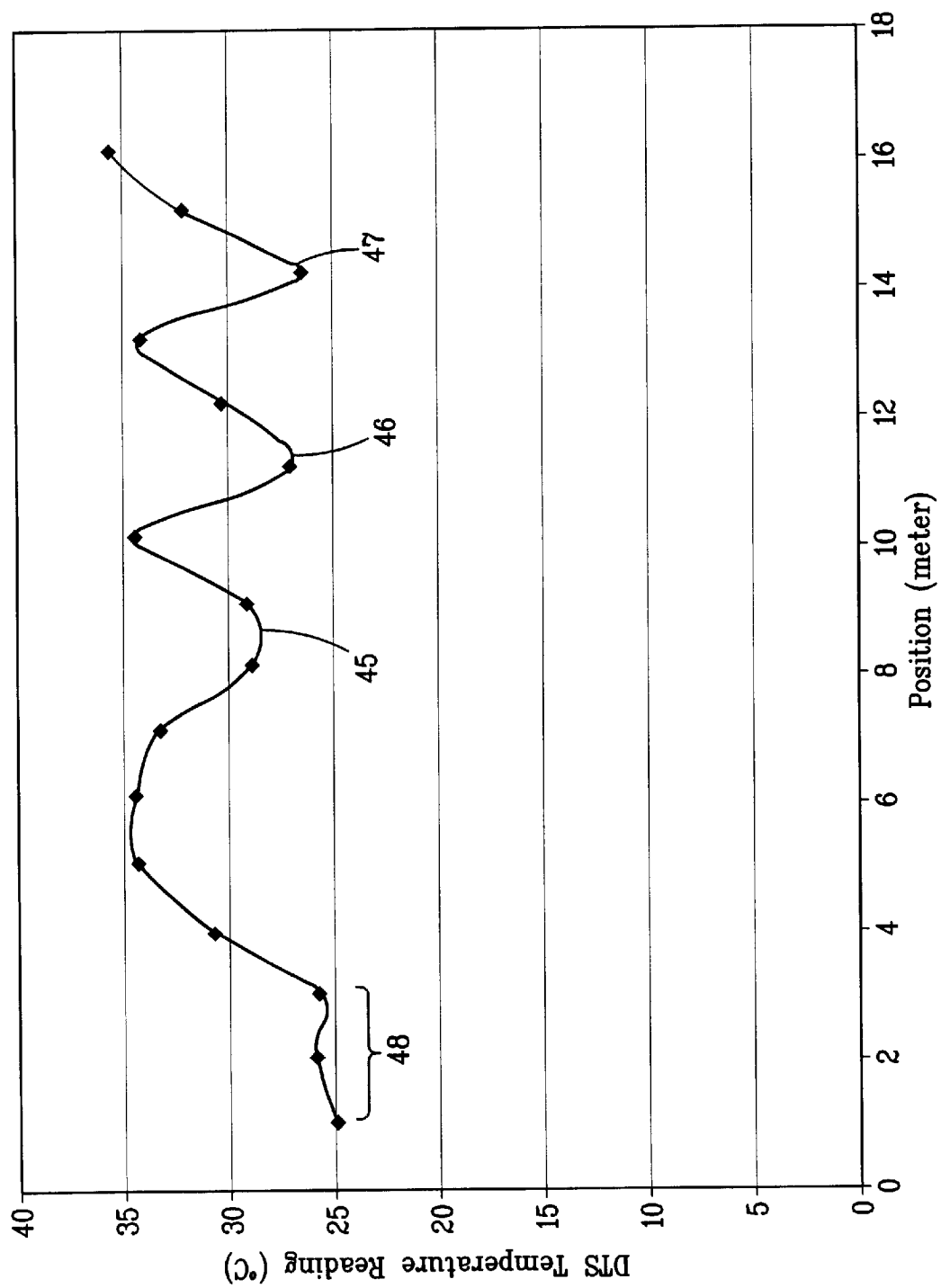

FIG. 4 shows the temperature data collected after wet towels were applied around three bends, and then heat was applied. Troughs (45, 36, 47) are apparent showing regions of lower temperature at positions of approximately 9, 11 and 14 meters, correlating to the bends where the wet towels were applied. (Note also that the figure shows another trough (48) in the region of the unheated lead-in portion of the cable.)

Figure 5:
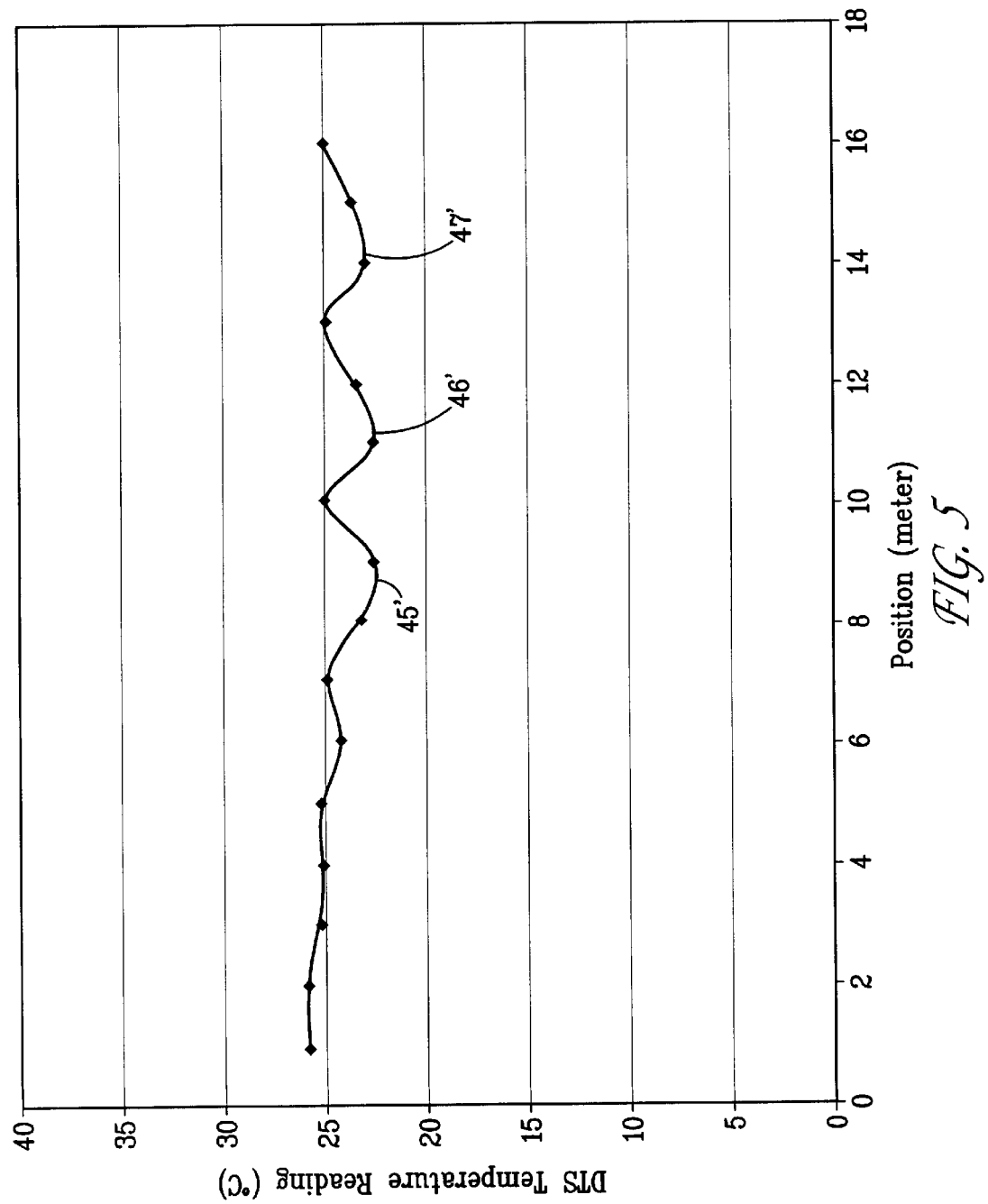
Figure 6:
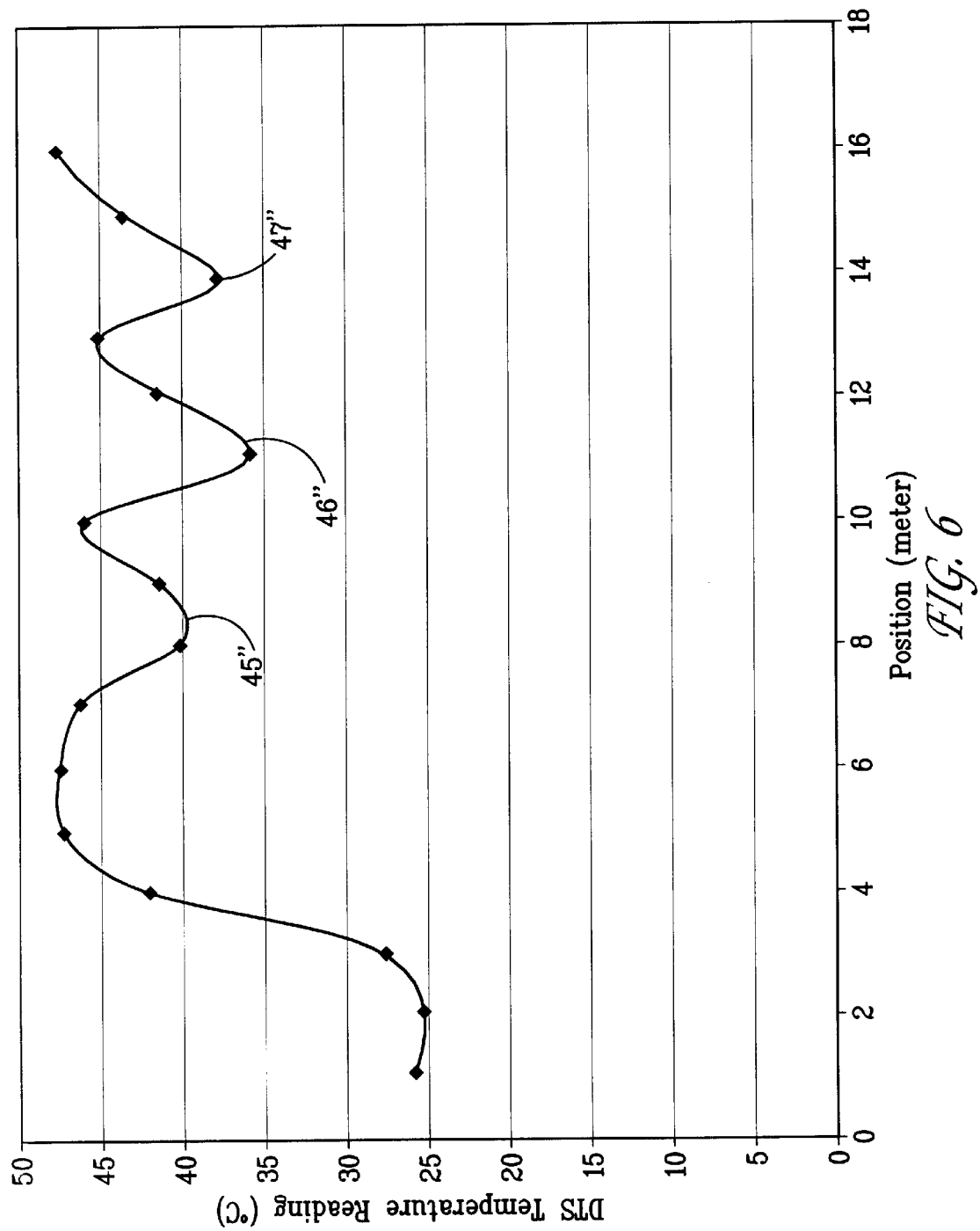

FIG. 5 shows readings from the same test arrangement as illustrated in FIG. 4, but in this case it is after the heater was turned off. Troughs (45', 46', 47') indicating positions of moisture are still apparent.

FIG. 6 shows readings, again from the same test arrangement, after heat is reapplied. Again, troughs (45", 46", 47") indicating positions of moisture are apparent.

Figure 7:
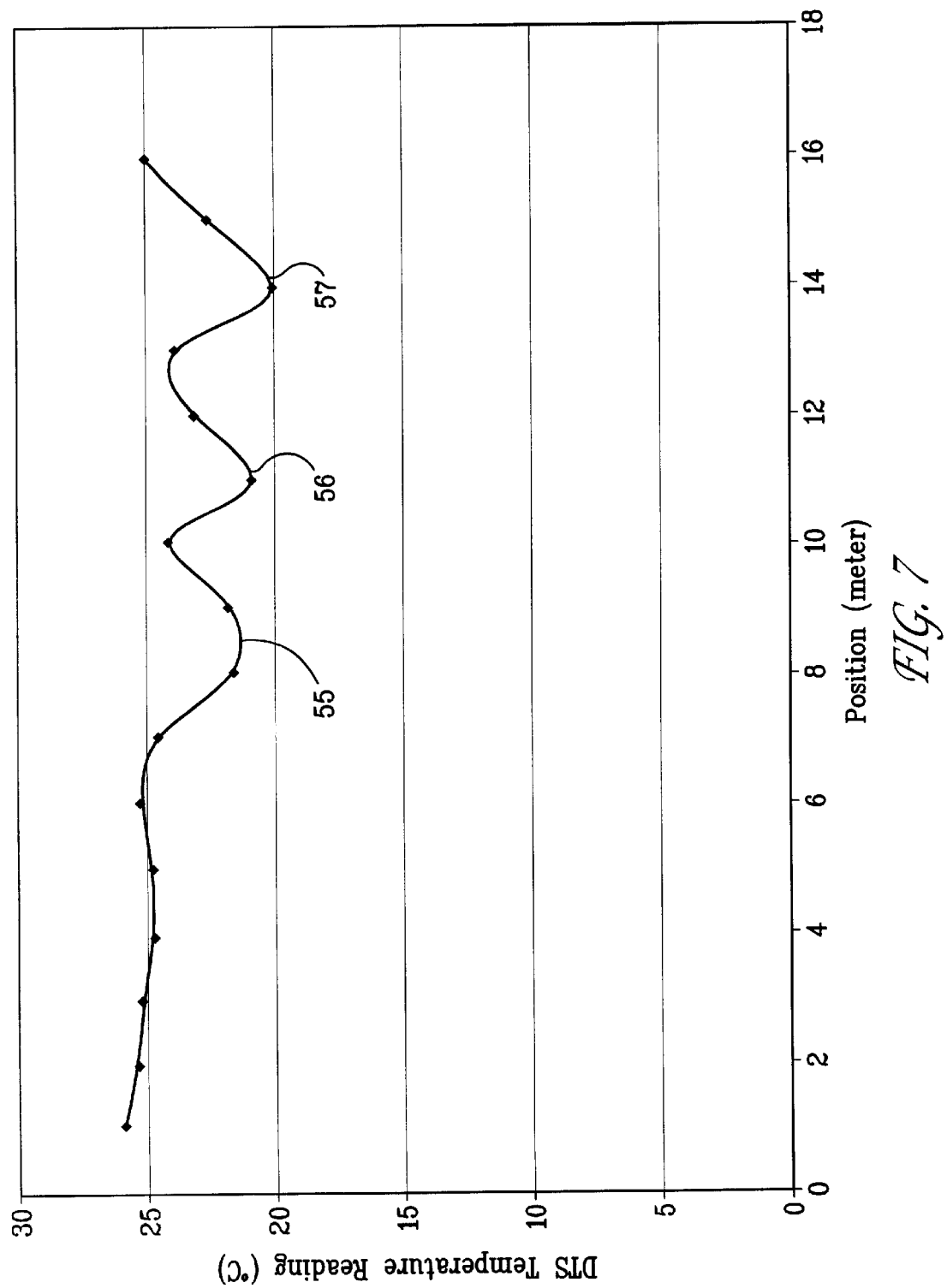

FIG. 7 shows readings taken after the system was allowed to stabilize at room temperature. Then slightly cool sand was poured over regions roughly corresponding to where the wet towels were applied previously. The effect of the cool sand is apparent from the troughs (55, 56, 57) depicted in the plot.

Figure 8:
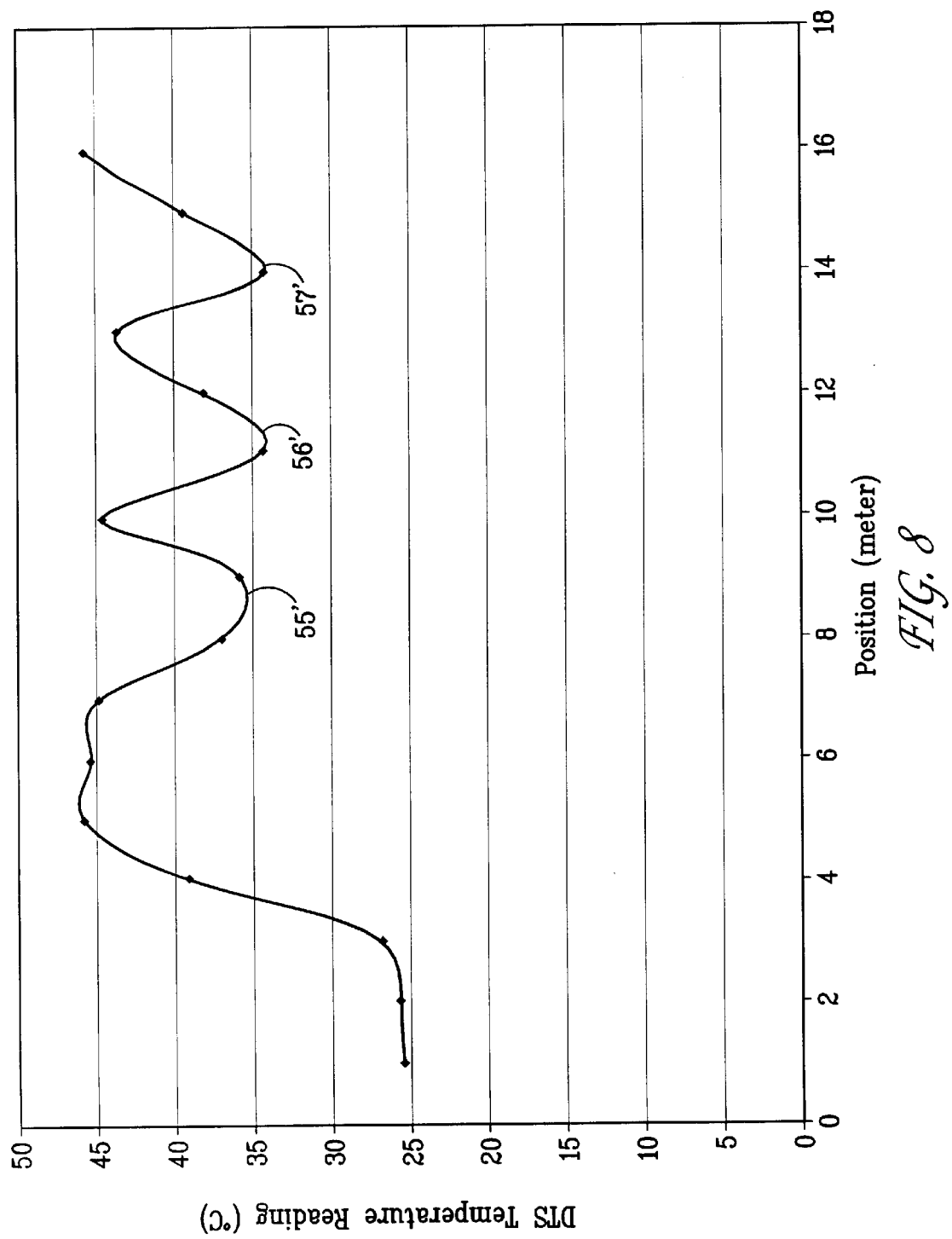

FIG. 8 shows readings taken after sand was applied as just described, and then water poured over the sand and heat applied. Troughs (55', 56', 57') indicating where the moisture is present causing differential response to heating are clearly apparent.

Figure 9:
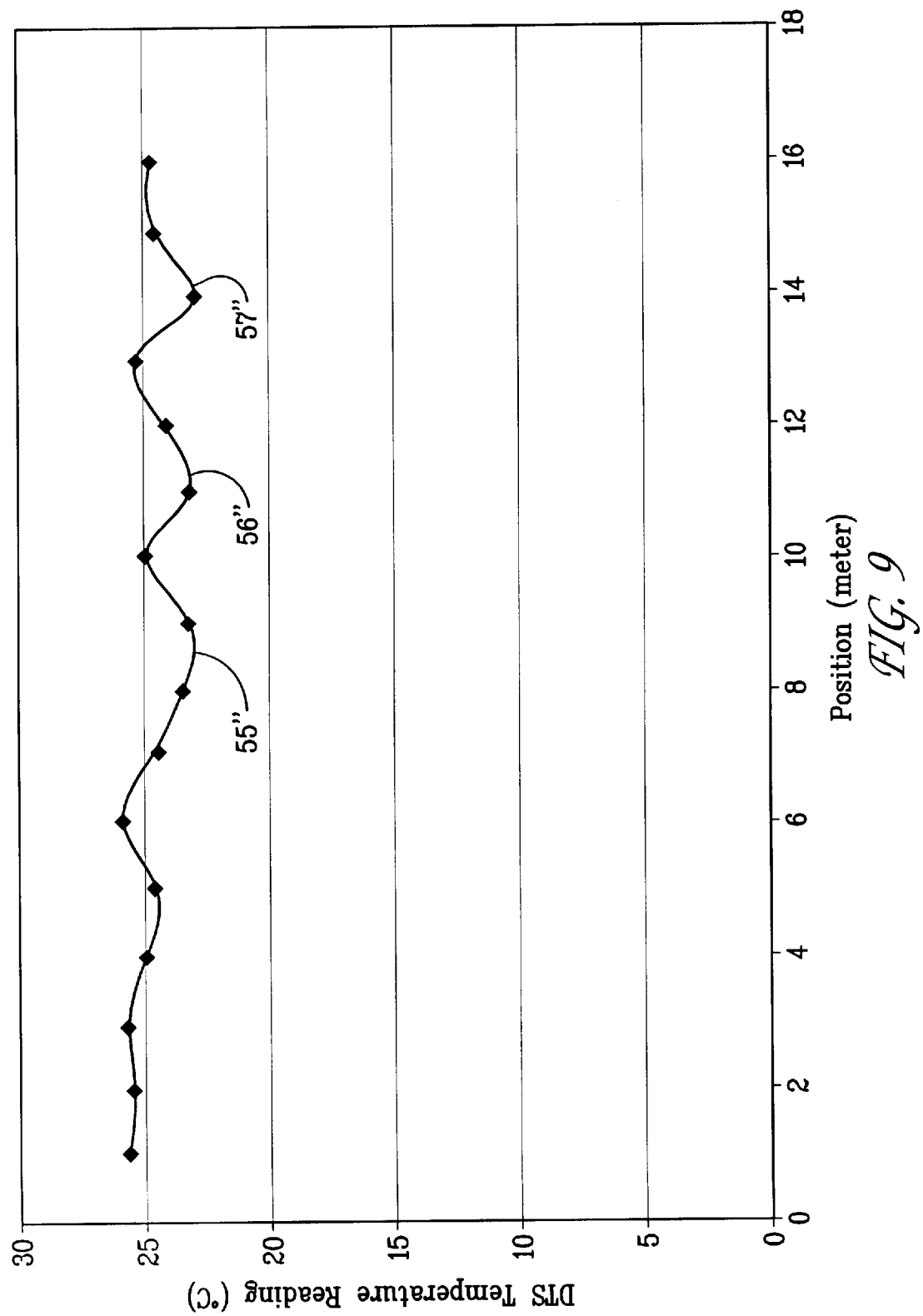

FIG. 9 shows temperature readings from the system after it is again allowed to cool. The effect of moisture is still apparent from the troughs (55", 56", 57").

Figure 10:
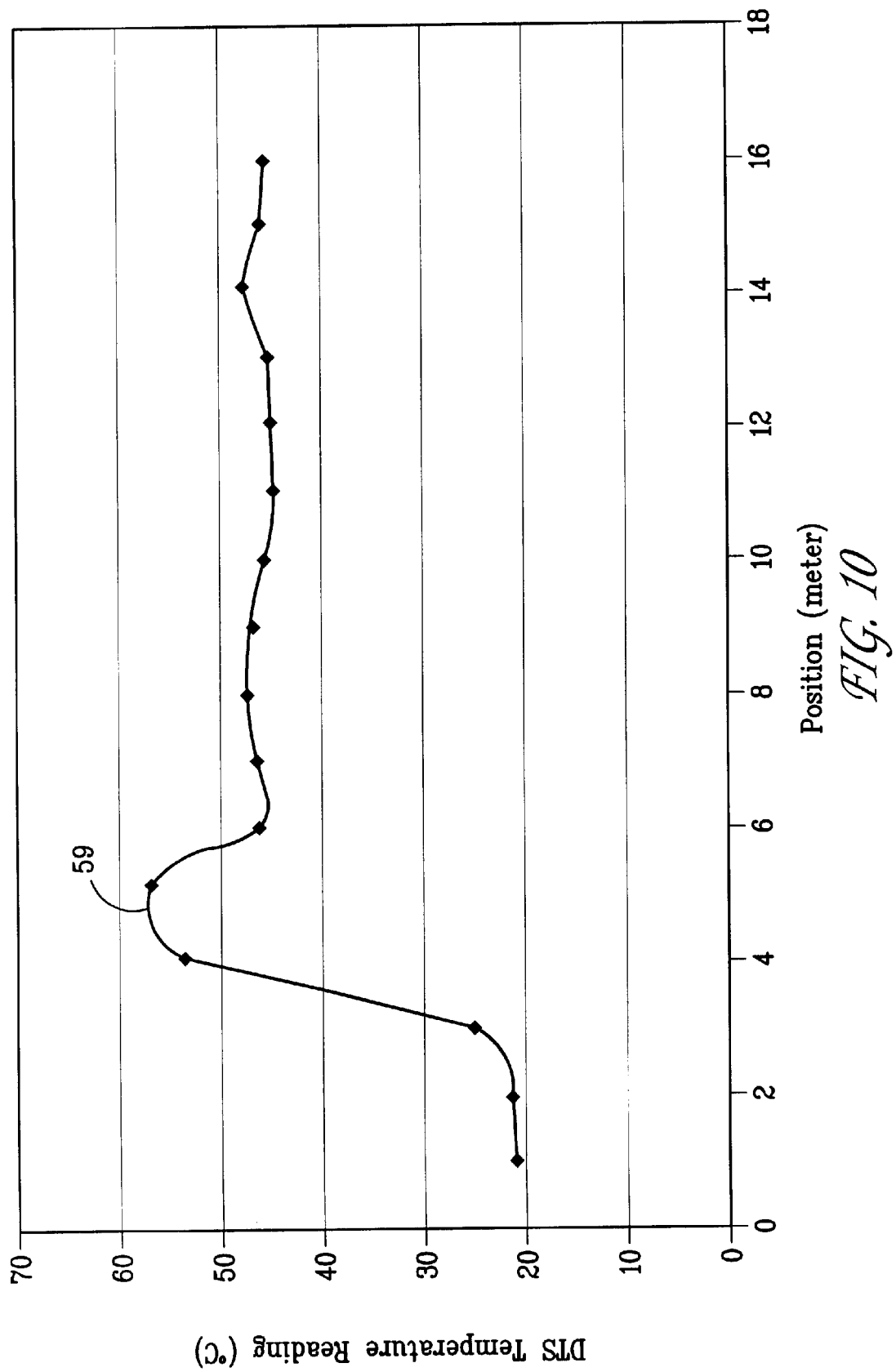

FIG. 10 shows readings after dry sand has been applied over almost the entire lengths of the cable. In this instance, heat is applied, but no moisture is added. The large peak 59 in the region of the 4-meter point on the cable shows that portion of the cable that was uncovered, preceded by a cool, unheated section of fiber. The slightly warmer section at around 14 meters is considered to probably be due to a fluctuation in the ambient temperature.

Figure 11:
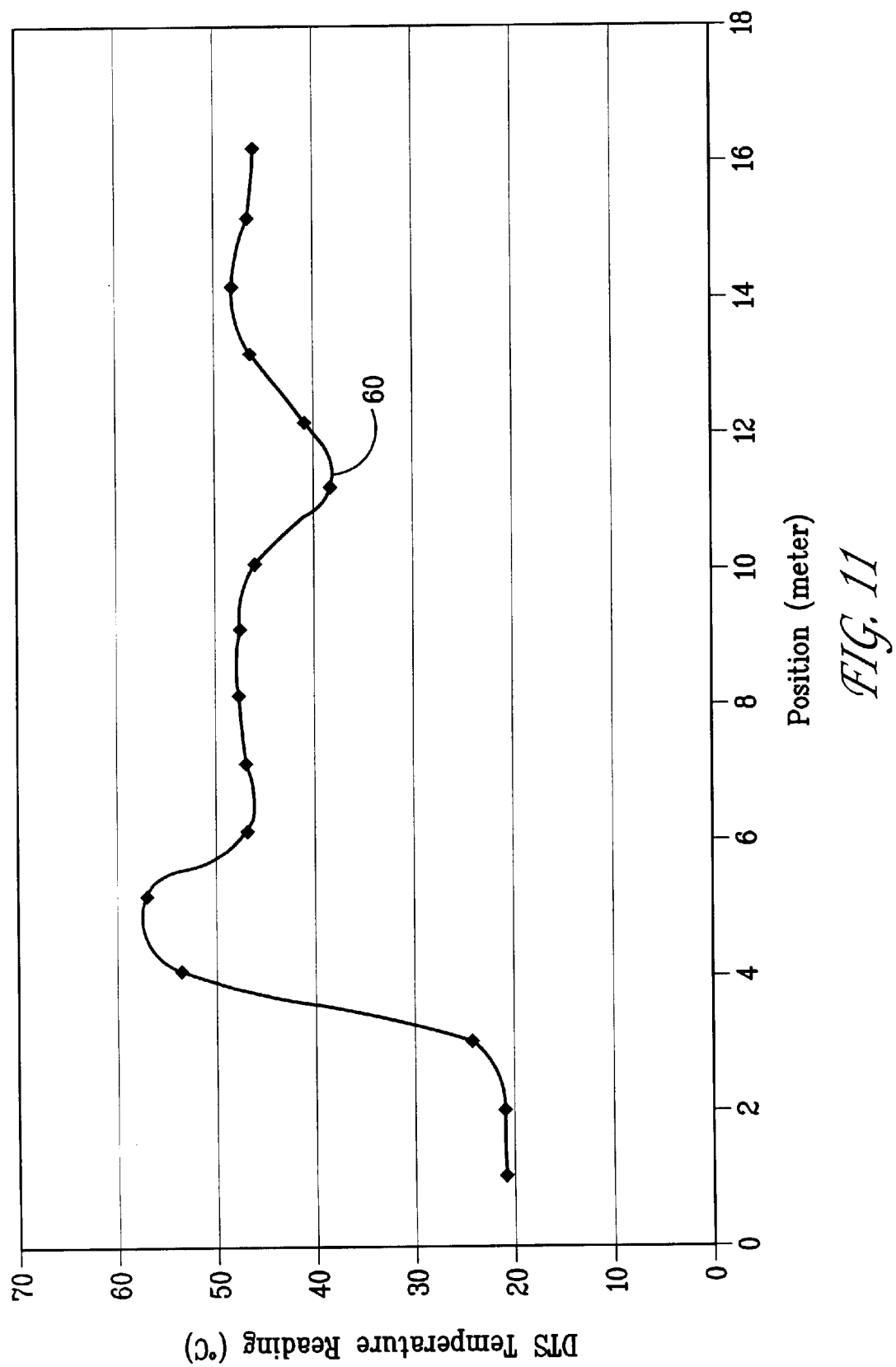

FIG. 11 shows the same system, with the heater on, after water is poured over sand covering the section of cable at about the 10-meter position. A trough (60) is apparent indicating the location of the moisture.

Figure 12:
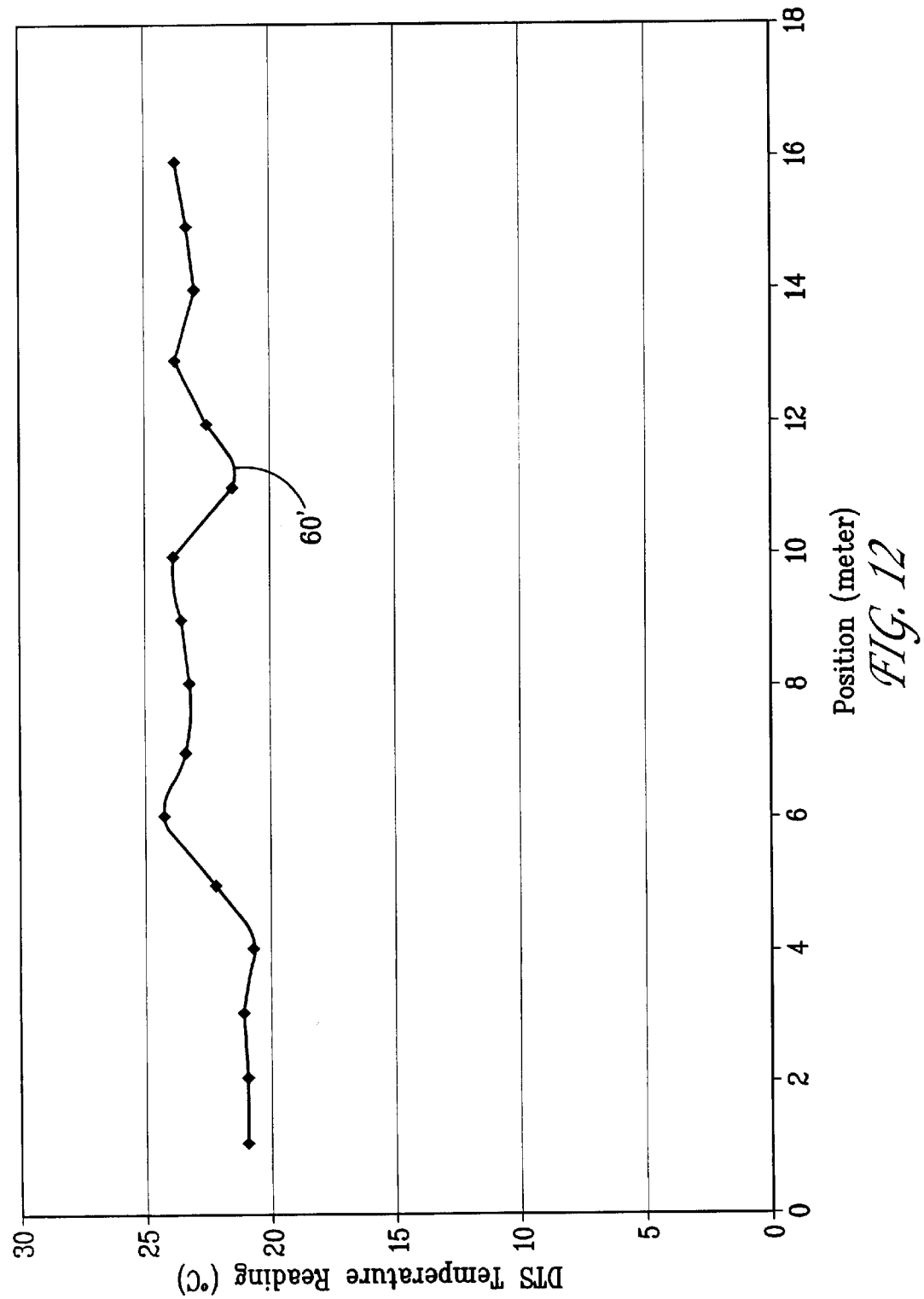

FIG. 12 shows the system after it has cooled almost to room temperature. The effect of moisture is still apparent from the presence of the trough (60').

Figure 13:
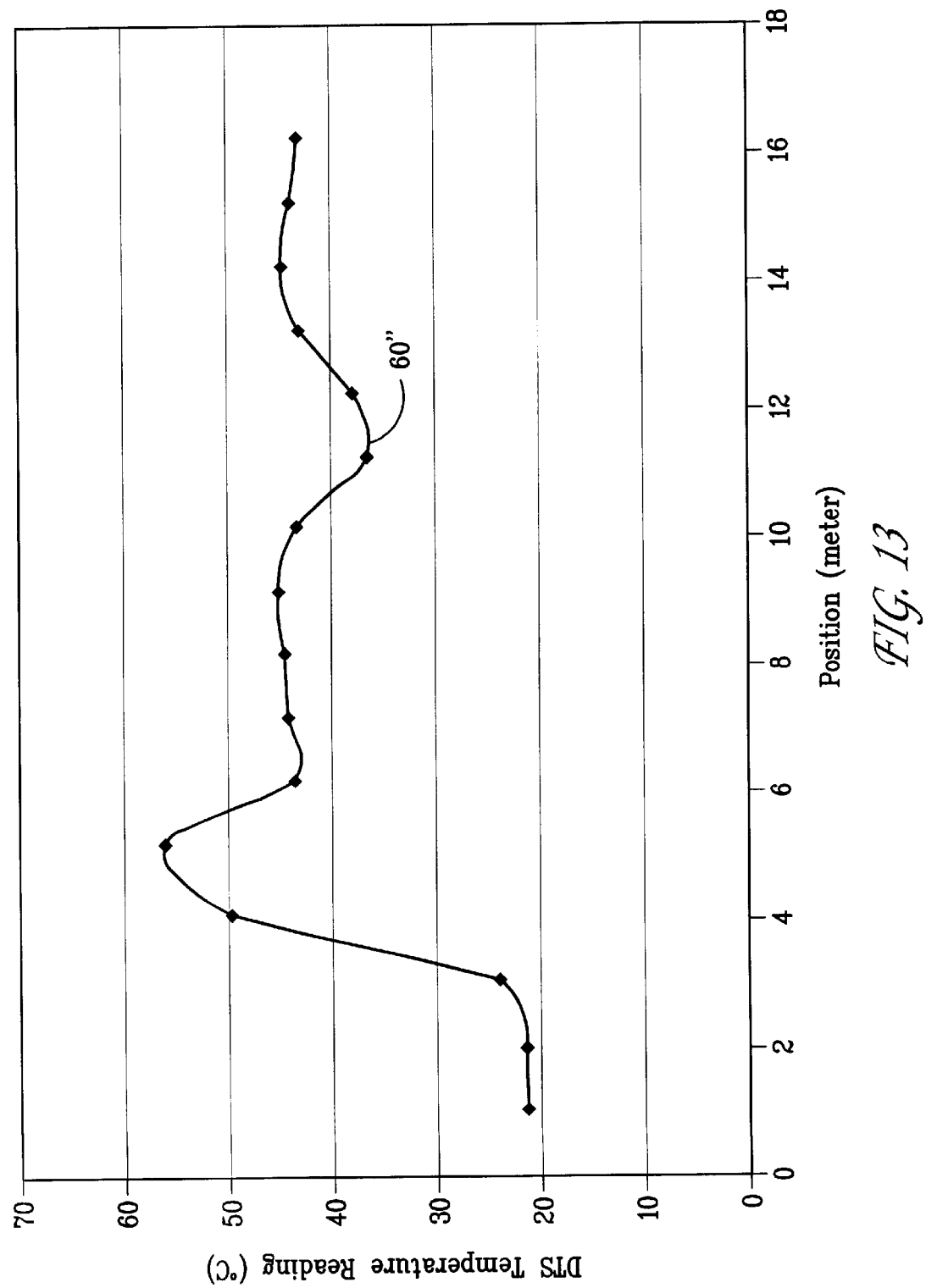

FIG. 13 shows the system after reheating. The presence of the trough (60") demonstrates that the effect of moisture is reproducible.

Figure 14:
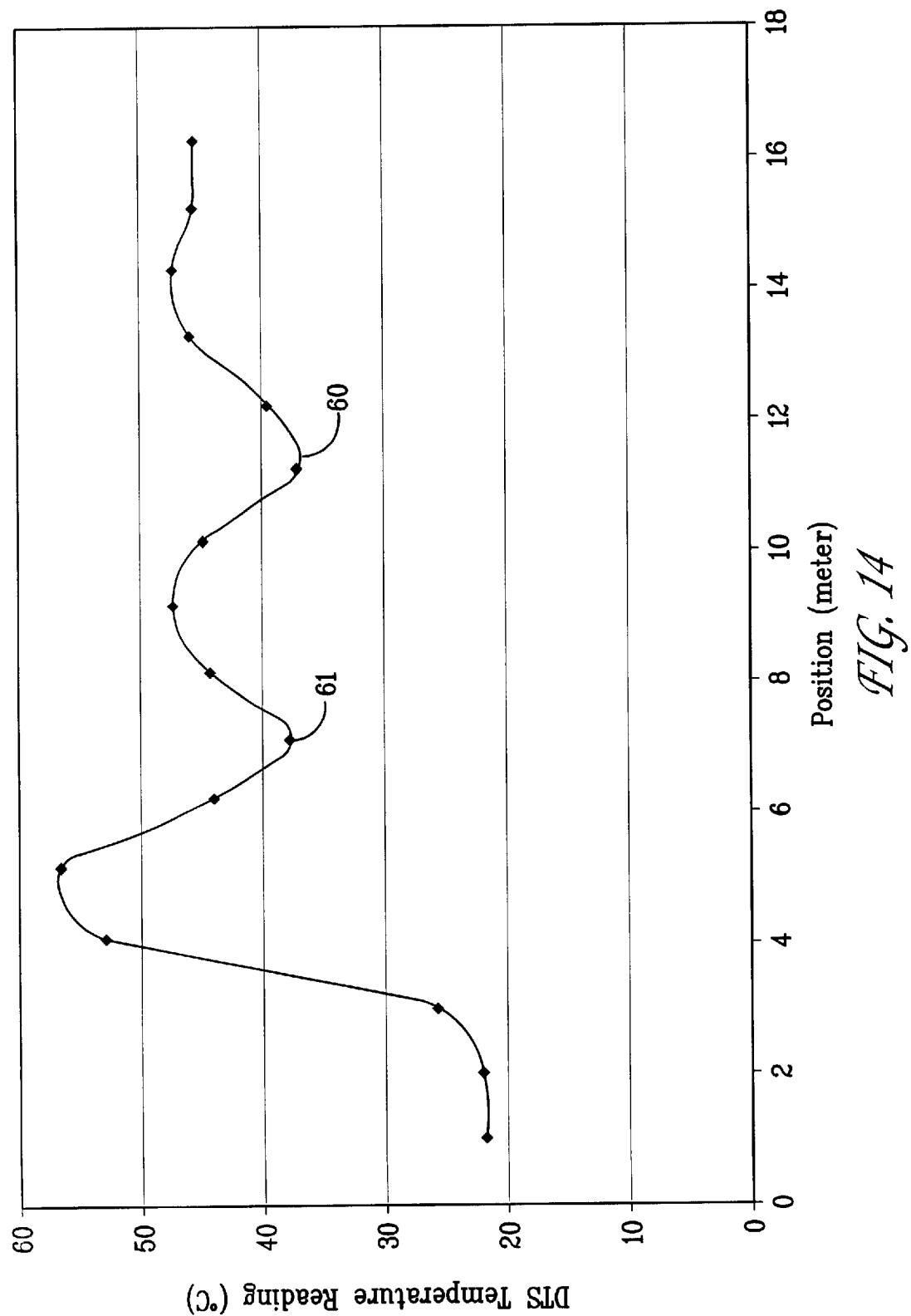

FIG. 14 shows the system, with heat still applied, with water poured over a second section. A second trough (61) is apparent at about 6 meters in addition to the previously identified trough (60) at about 11 meters. This indicates that moisture in separate regions of the volume of sand are independently identifiable using the invention.

Figure 15:
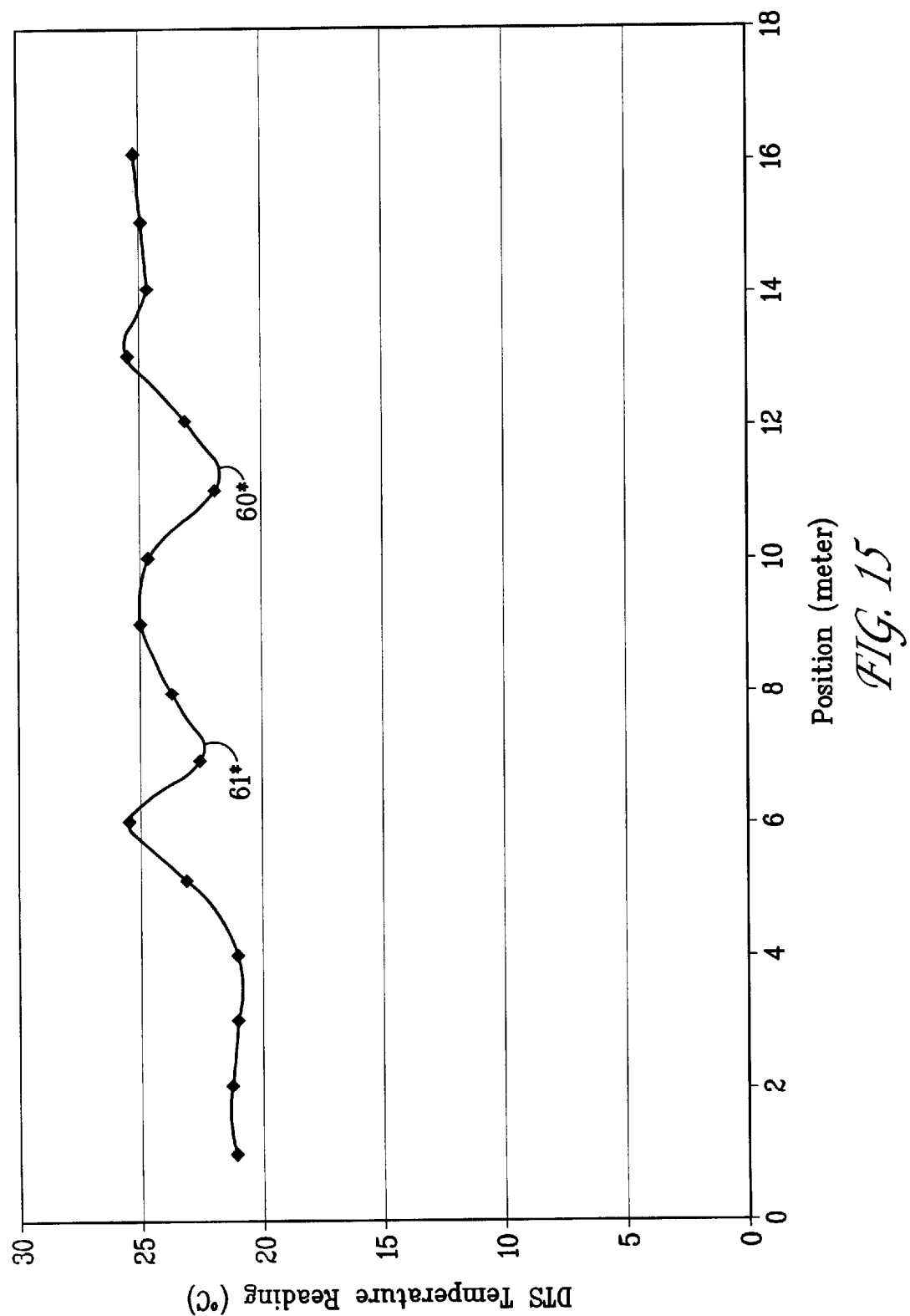

FIG. 15 shows the system after it has been allowed to cool. The effect of the moisture in the two regions is still apparent from the two troughs (**60\*, 61\***). Also apparent from the plot is the insulating effect of the sand, which keeps covered sections slightly warmer than the uncovered lead-in.

Figure 16:
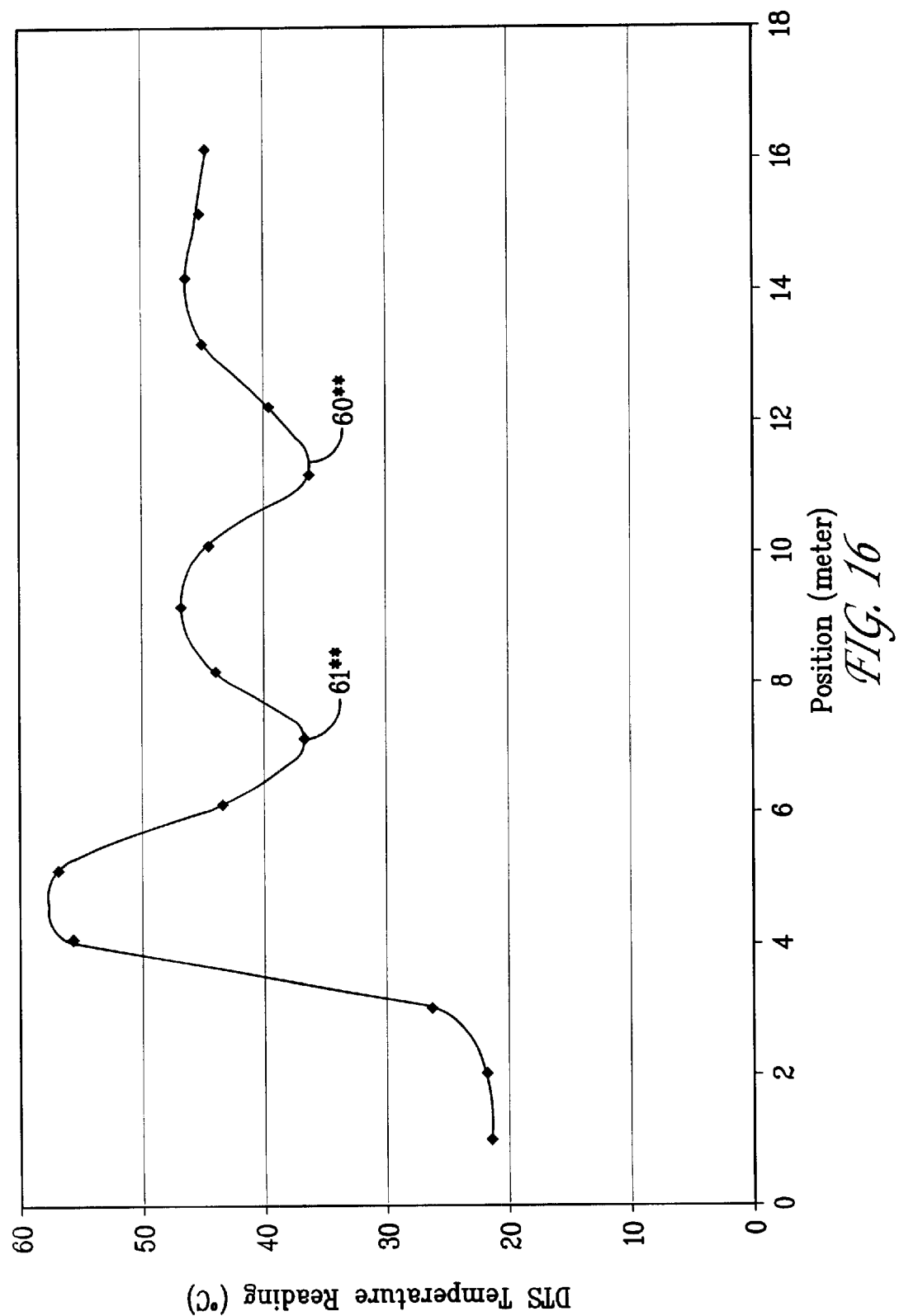

FIG. 16 shows, finally, the effect of reheating, and illustrates that the effect of moisture on the two sections is still apparent from the troughs (**60\*\*, 61\*\***). The previously cooler lead-in is now warmer than the covered length of the cable. It is preceded by an unheated section of fiber.

Figure 2B:
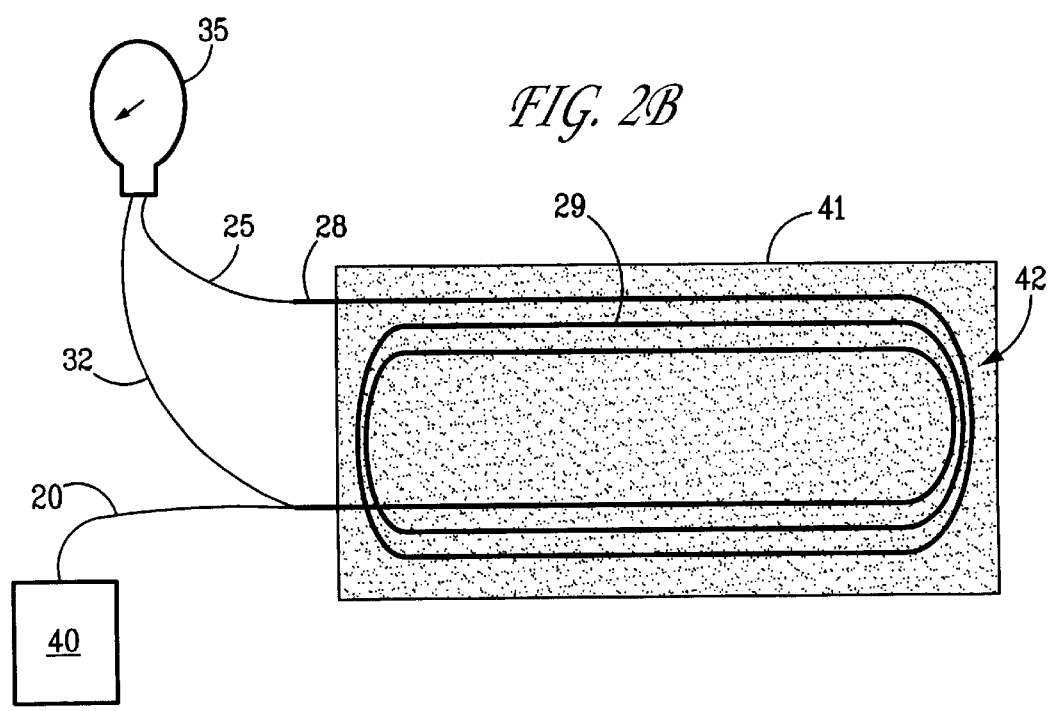
FIG. 2b is a schematic depiction of an apparatus according to the invention wherein coils comprising heating and temperature sensing elements are positioned within a volume of sand.

FIGS. 17–26 correspond to tests performed using the test configuration illustrated schematically in FIG. 2b which shows an alternate experimental set up wherein stainless steel tubing was used to house the fiber optic. In this instance a hybrid cable similar to that used before and comprising both an optical fiber 20 and a heater wire 25 within tube 28 is used, however this time the cable is inserted into a coil of stainless steel tubing 29 positioned in a tray 41. As before, the heater wire 25 is connected to the variac 35, directly at one end, and via an electrical lead 32 at the other, and the optical fiber 20 is in operative association with a commercial DTS data acquisition and processing unit 40. Assume that, for purposes of the following description of the figures, when moisture was applied that it occurred in the region 42 shown.

Figure 17:
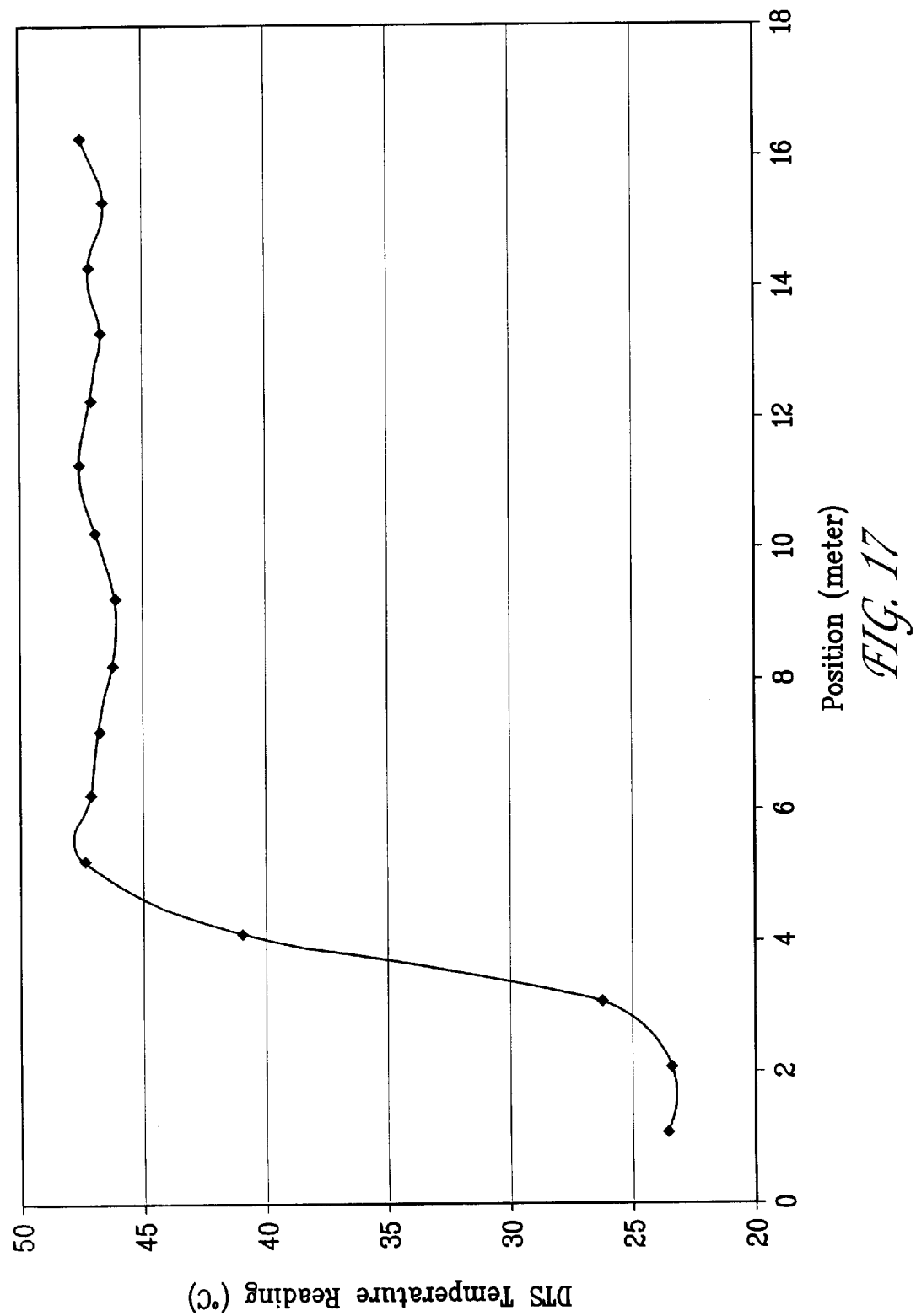

FIG. 17 shows readings for the cable inserted in the stainless steel tubing. Heat has been applied in the absence of water or sand. Random variations in temperature are apparent along the length of the fiber.

Figure 18:
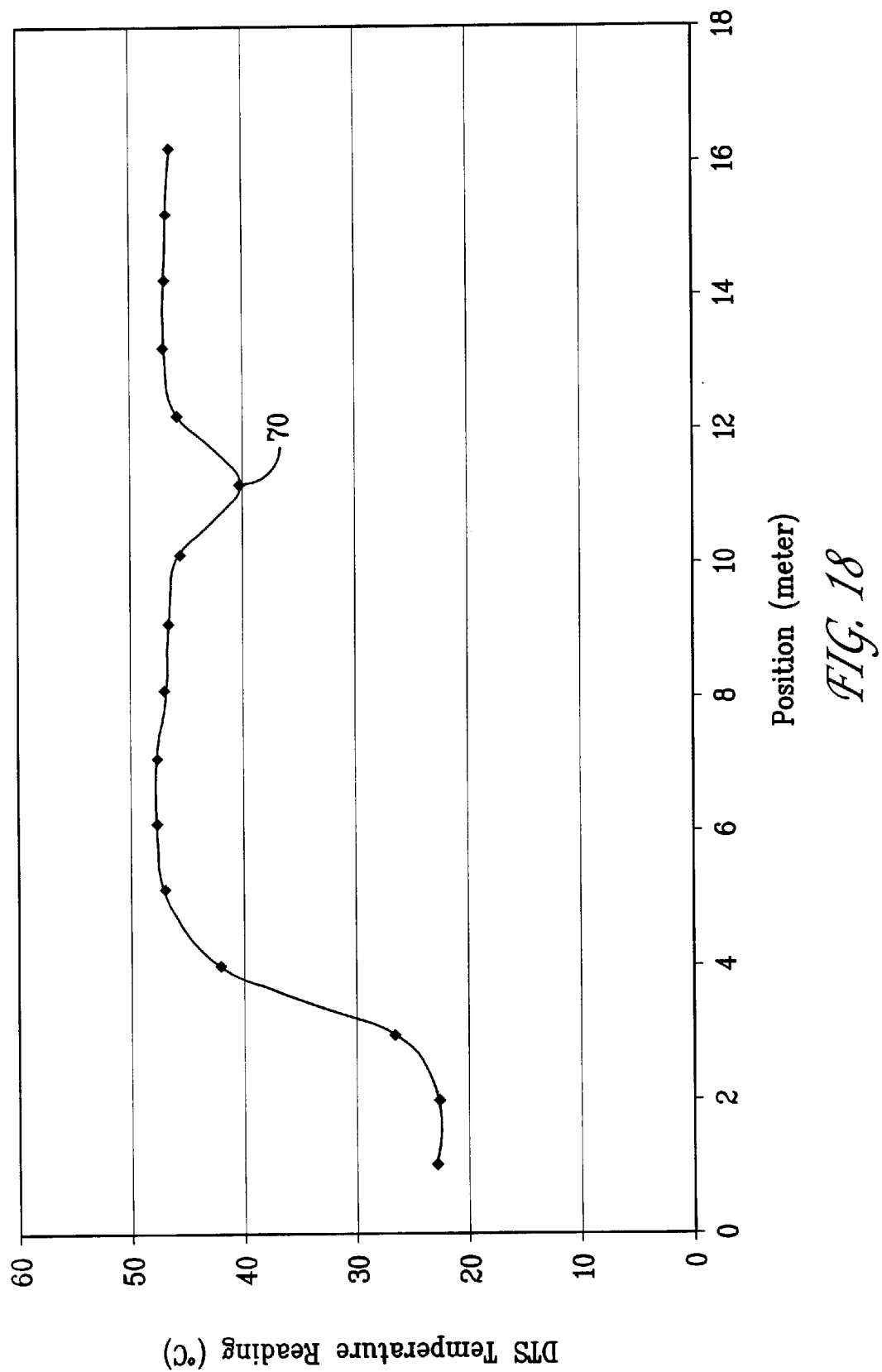

FIG. 18 shows results when, with the heat still on (and no sand), a wet towel is applied directly to one section of tubing. The trough (70) at approximately 11 meters shows that thermal conductance of the tube has not significantly diffused the heat along it. Any "dead air" space in the tube has not produced a noticeable thermal barrier.

Figure 19:
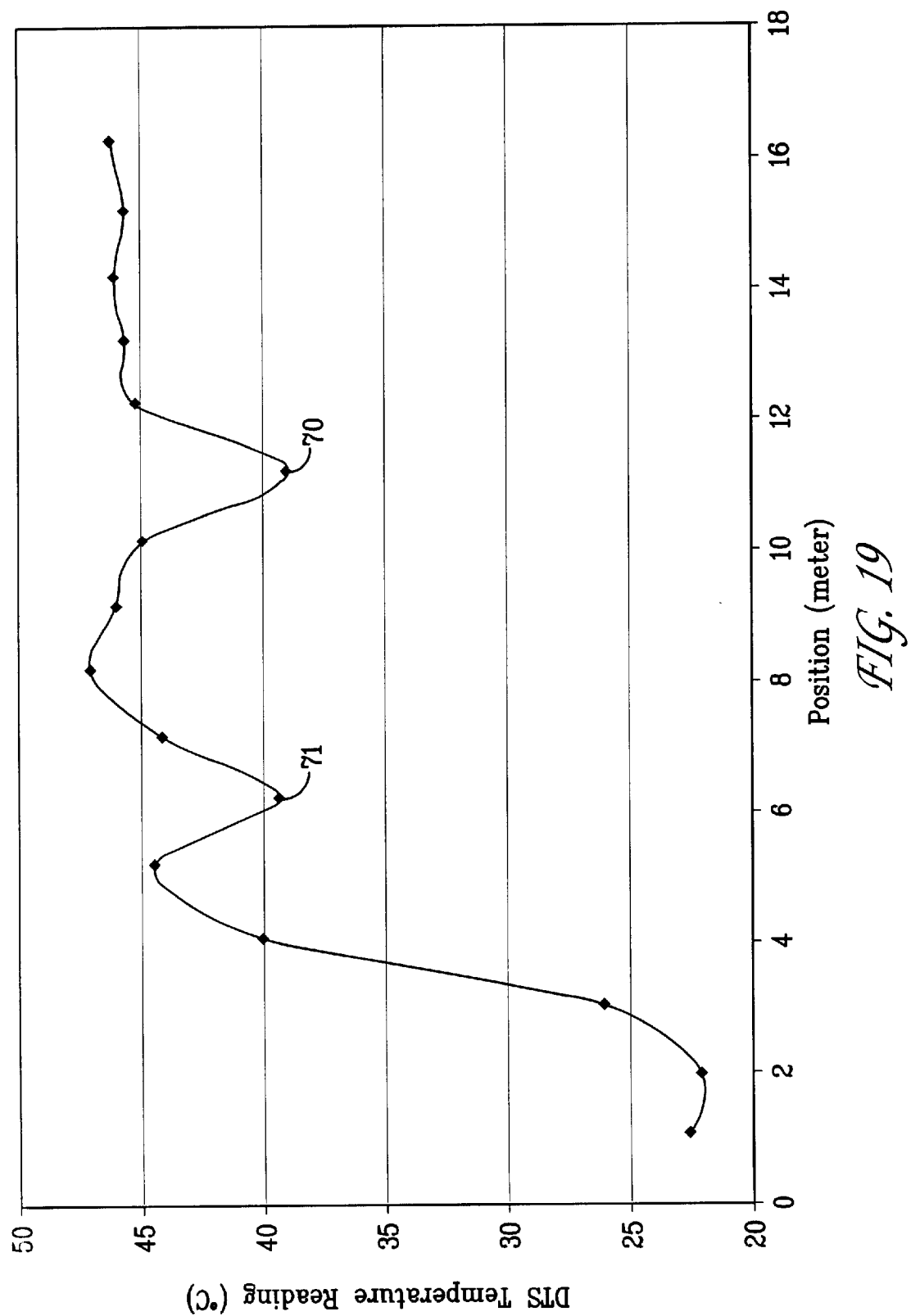

FIG. 19 shows readings for the same configuration just described, but with another wet towel applied to a second spot. The trough (71) at approximately 5 meters indicates where the cooling effect of the second towel was registered by the DTS system.

Figure 20:
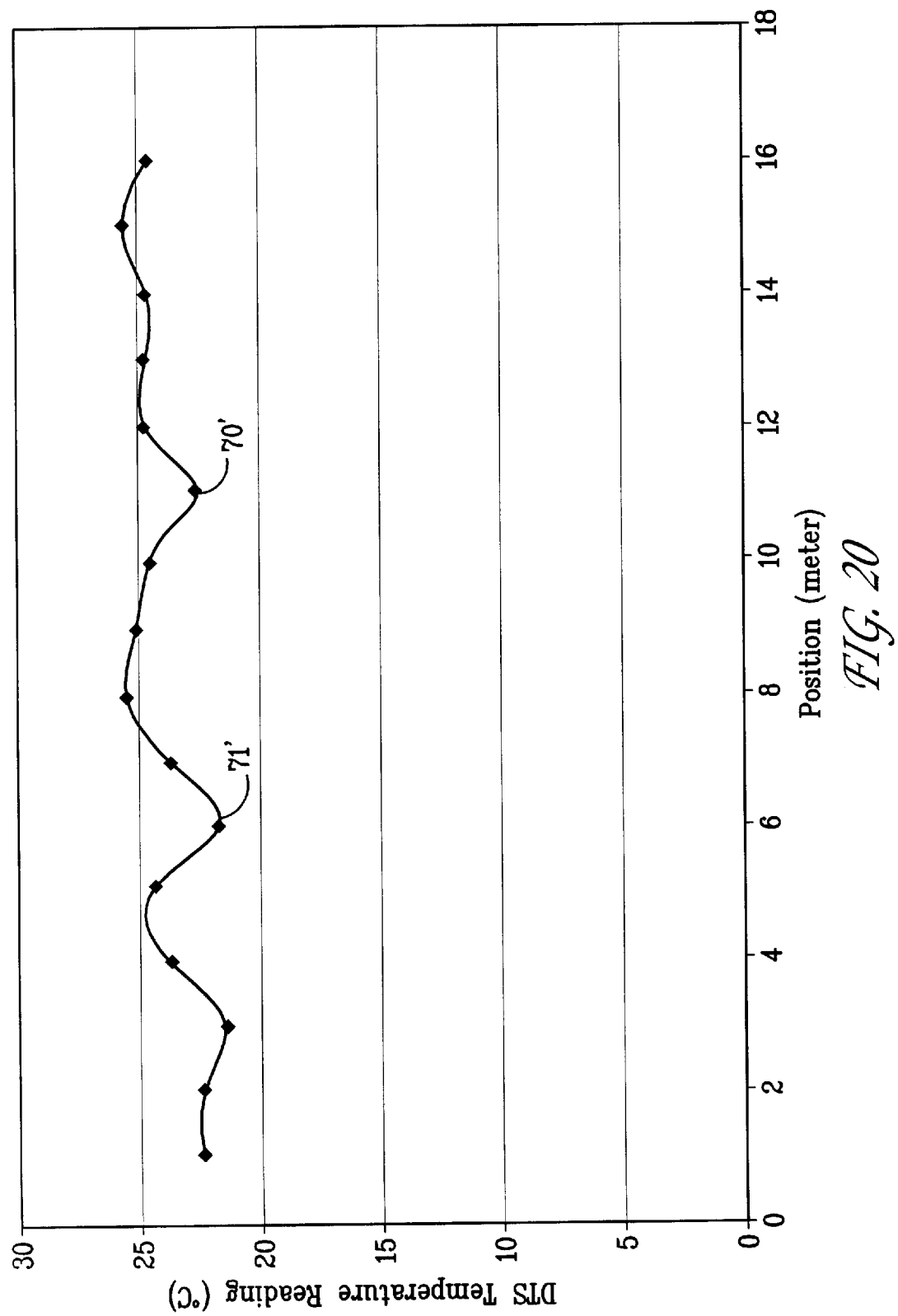

FIG. 20 shows the same system after it has nearly cooled to room temperature. The effect of the two wet regions is still evident from the two troughs.(70', 71'). The slight dip in the lead-in section is probably due to an ambient fluctuation.

Figure 21:
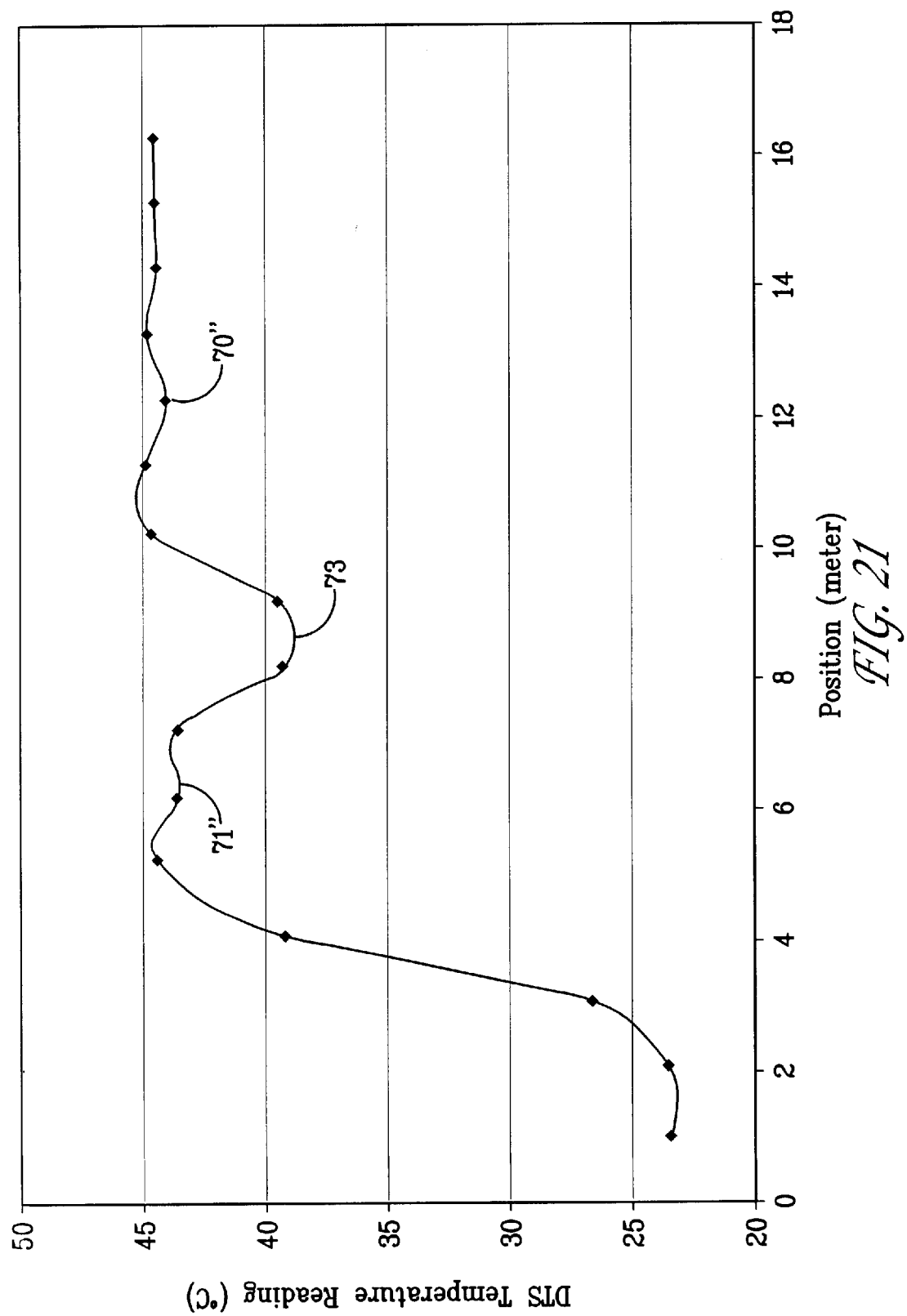

FIG. 21 shows the system after the towels are removed and sand is added in the region of about 7 meters. The system is heated, but no water is added. A trough (73) is apparent showing cooing associated with the application of the sand. This cooler region is due to the heat capacity of the sand. The residual effect of the towels is also apparent from the troughs (70", 71").

Figure 22:
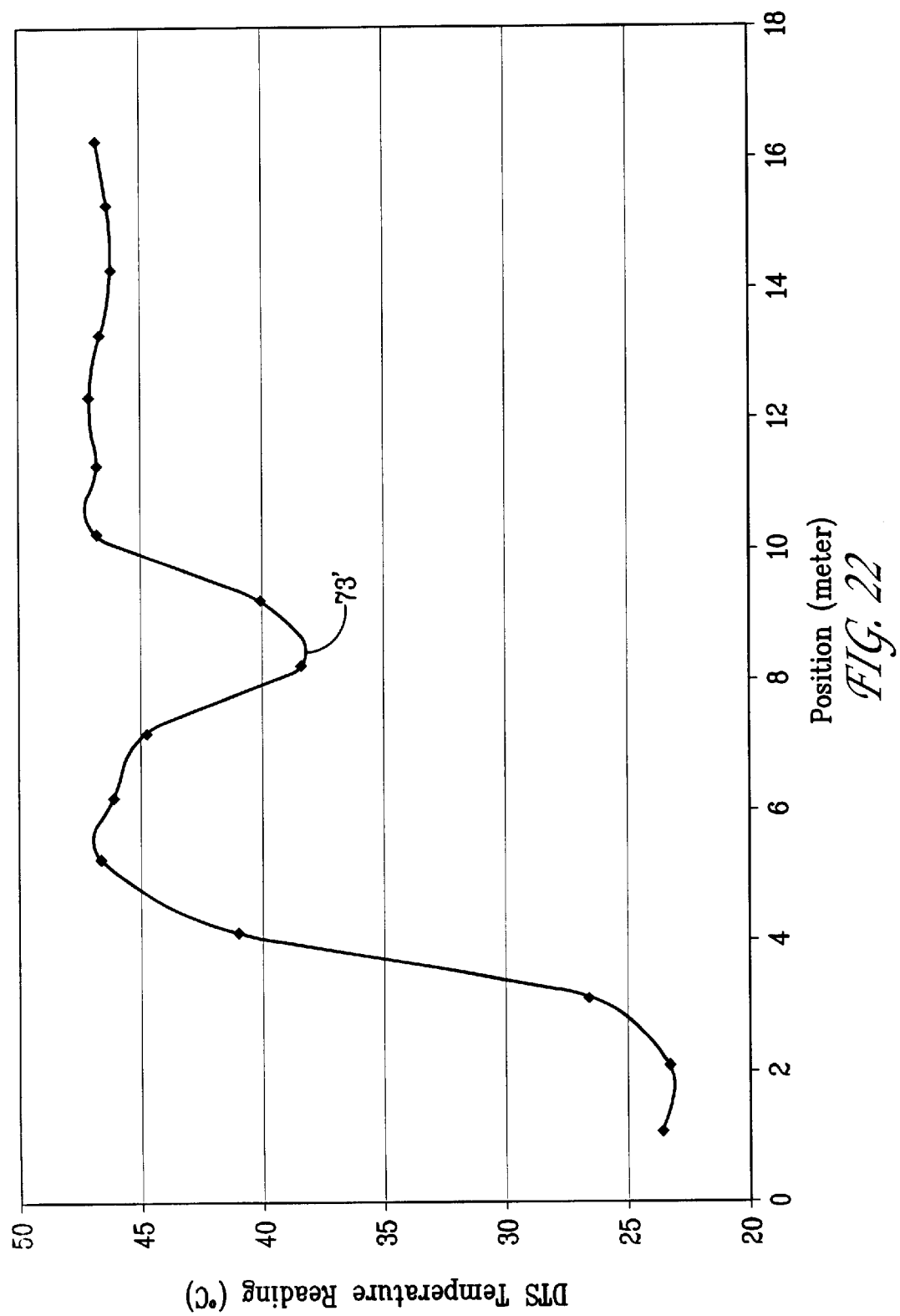

FIG. 22 shows the system with the heat still on, after water was added over the sand at approximately 7 meters. The trough (73') indicates enhanced cooling of that section of the cable.

Figure 23:
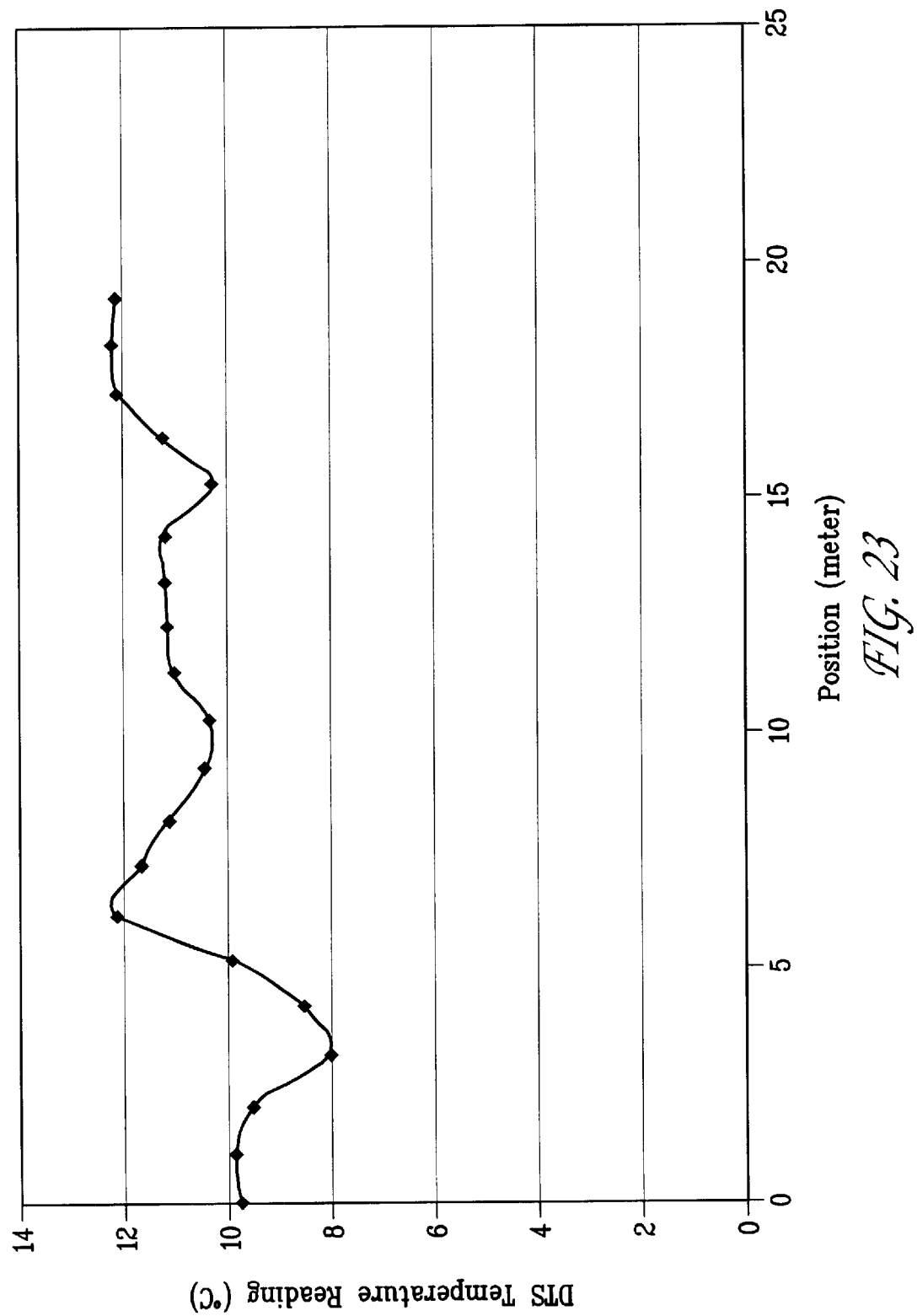

FIG. 23 shows results of a baseline measurement with the fiber and heater inside stainless steel tubing completely buried in a sandbox (with the exception that both end sections were left uncovered). In this test, the measurements were taken outside rather than inside the interior of a building, as was done for the previously discussed results. Temperature variations are apparent due to the unevenness of the plot, however the temperature variations are not surprising due to the less controlled environment. For this plot, neither heat nor water is applied.

Figure 24:
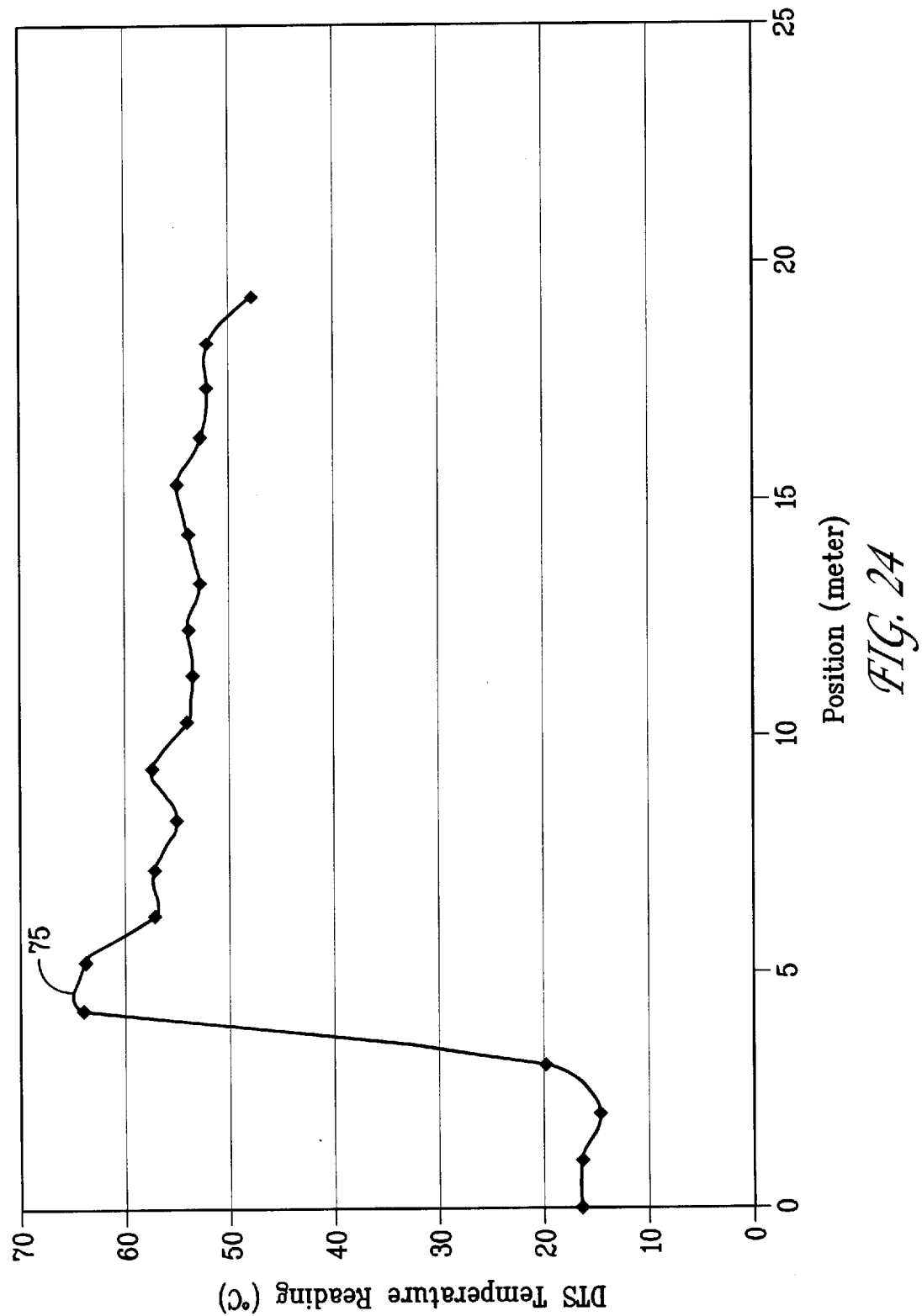

FIG. 24 shows results when heat is applied to the dry sand in the system configuration just described. An unheated portion of fiber optic precedes a peak (75) representing a hot section outside of the sand.

Figure 25:
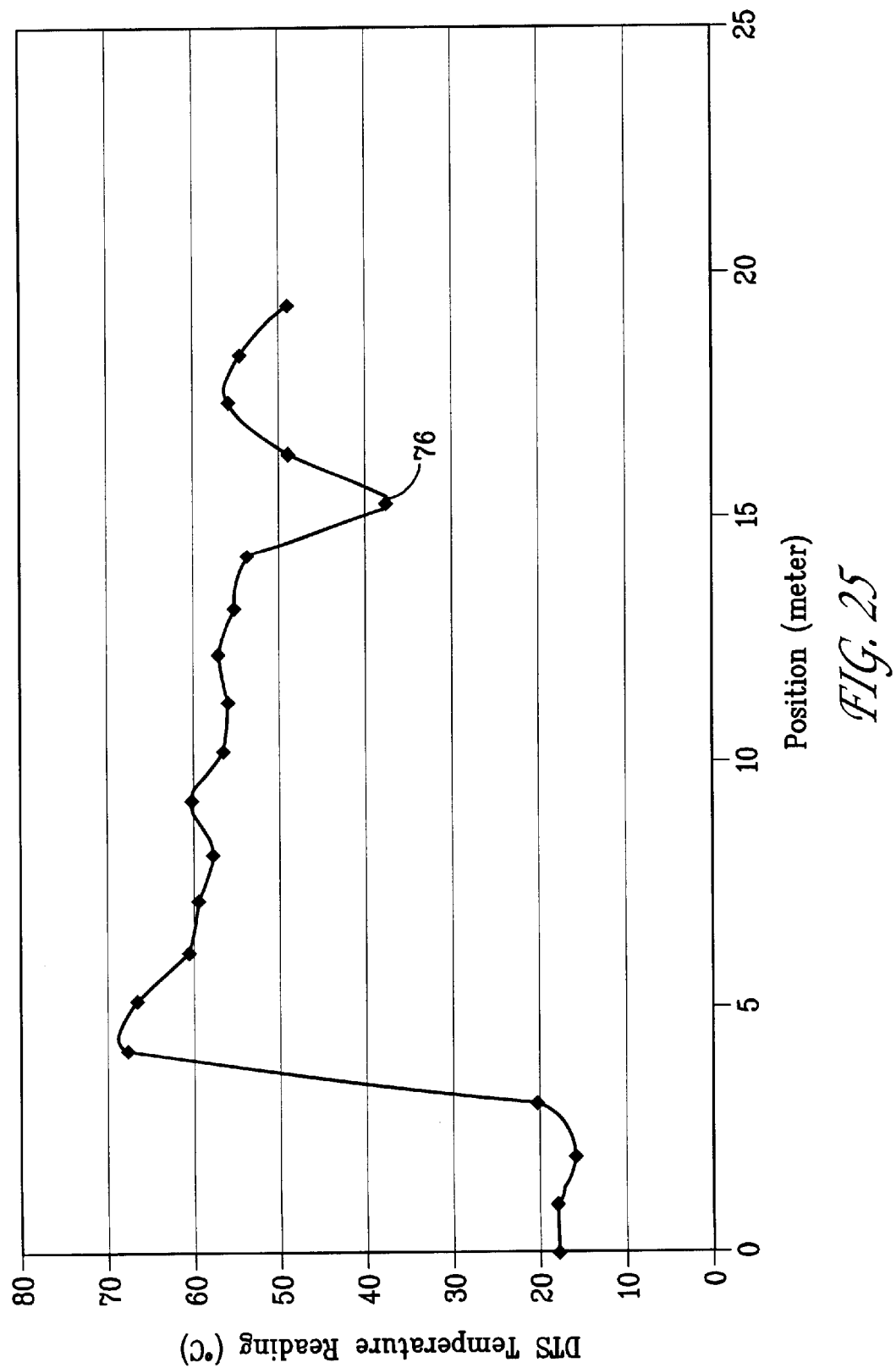

FIG. 25 shows the results from the system with heat applied and water applied over one section of sand. Cooling is apparent from the trough (76) at approximately 15 meters.

Figure 26:
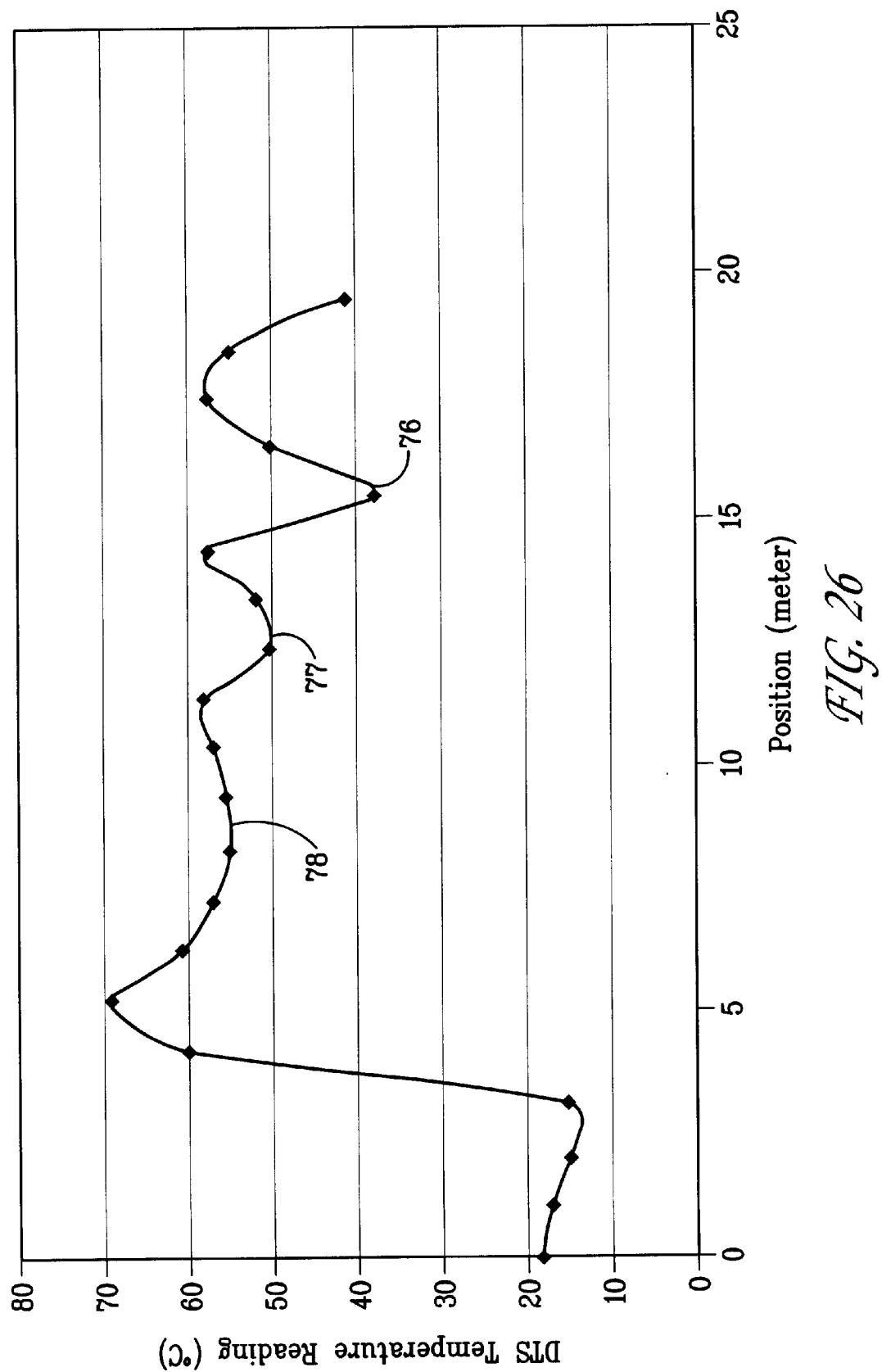

FIG. 26 illustrates results where more water is added over the same section. This forces water to contact two loops positioned below the loop closest to the top in the sandbox. As would be expected, the effect diminishes in strength and becomes more diffuse at lower levels indicated by troughs (77, 78) correlating to those portions of the cable at about 11 meters and about 7 meters (but positioned, as noted, at a greater depth within the sandbox. These results, though, show that successful tracking of the progression of moisture moving through a three-dimensional space can be accomplished using the invention.

Figure 27:
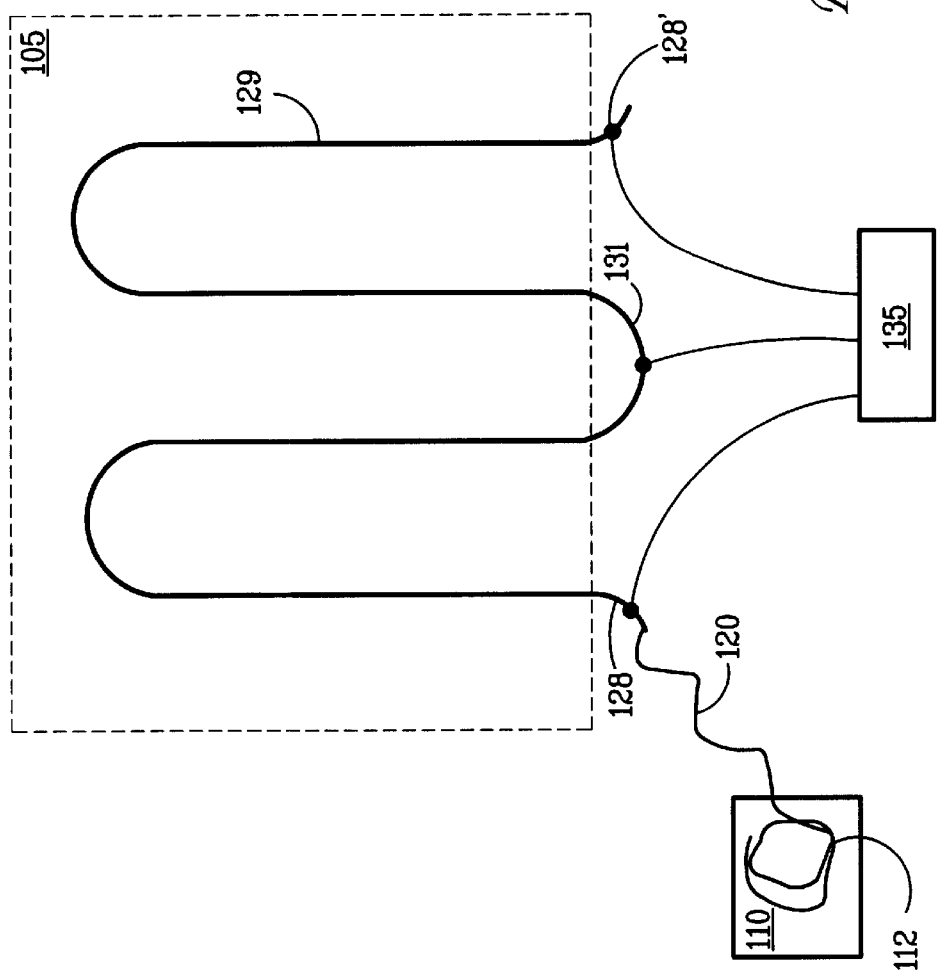
FIG. 27 is a schematic depiction of an apparatus according to the invention wherein a sensor within a stainless steel tube is positioned in soil.

The remaining discussion that follows describes an intermediate-scale test of the inventive moisture intrusion sensor system that has been conducted to examine its performance under more realistic circumstances than the small-scale tests already discussed. The intermediate-scale test also verifies the use of the conduit as a heater, as well as a protective enclosure for the fiber. FIG. 27 illustrates the basic arrangement for the test. It shows the DTS system 110, inside of which is a so-called reference coil 112 maintained quite accurately in a chamber at 100 F. This 150-ft-long coil is necessary to convert raw signal to temperature according to principles known to those skilled in the art of distributed temperature sensing. Immediately outside the DTS system 110 is approximately 125 feet of optical fiber 120 connecting the DTS system 110 to the length of stainless-steel enclosed fiber 129. (In this case, the stainless-steel enclosed fiber is a length of optical fiber housed inside a stainless steel tube.) The stainless-steel enclosed fiber 129 serves as the sensor element which runs in a serpentine fashion within a volume of soil 105 (viewed from above, in the Figure) about three feet under the soil surface. About half way along the sensor a short length 131 of the stainless steel tube emerges above the surface of the soil to serve as an electrically common point for the power supply 135. At either end of the tube is also a short length 128, 128' above ground to allow for electrical connections. The entire length of optical fiber is about 750 feet. It should be noted that no attempt was made to achieve uniformity of the soil constituents nor uniformity of its moisture content. In fact, it had rained shortly before the test was conducted, and the test was begun only when the surface had dried out. Thus, for this test, the soil was basically uncontrolled.

Figure 28:
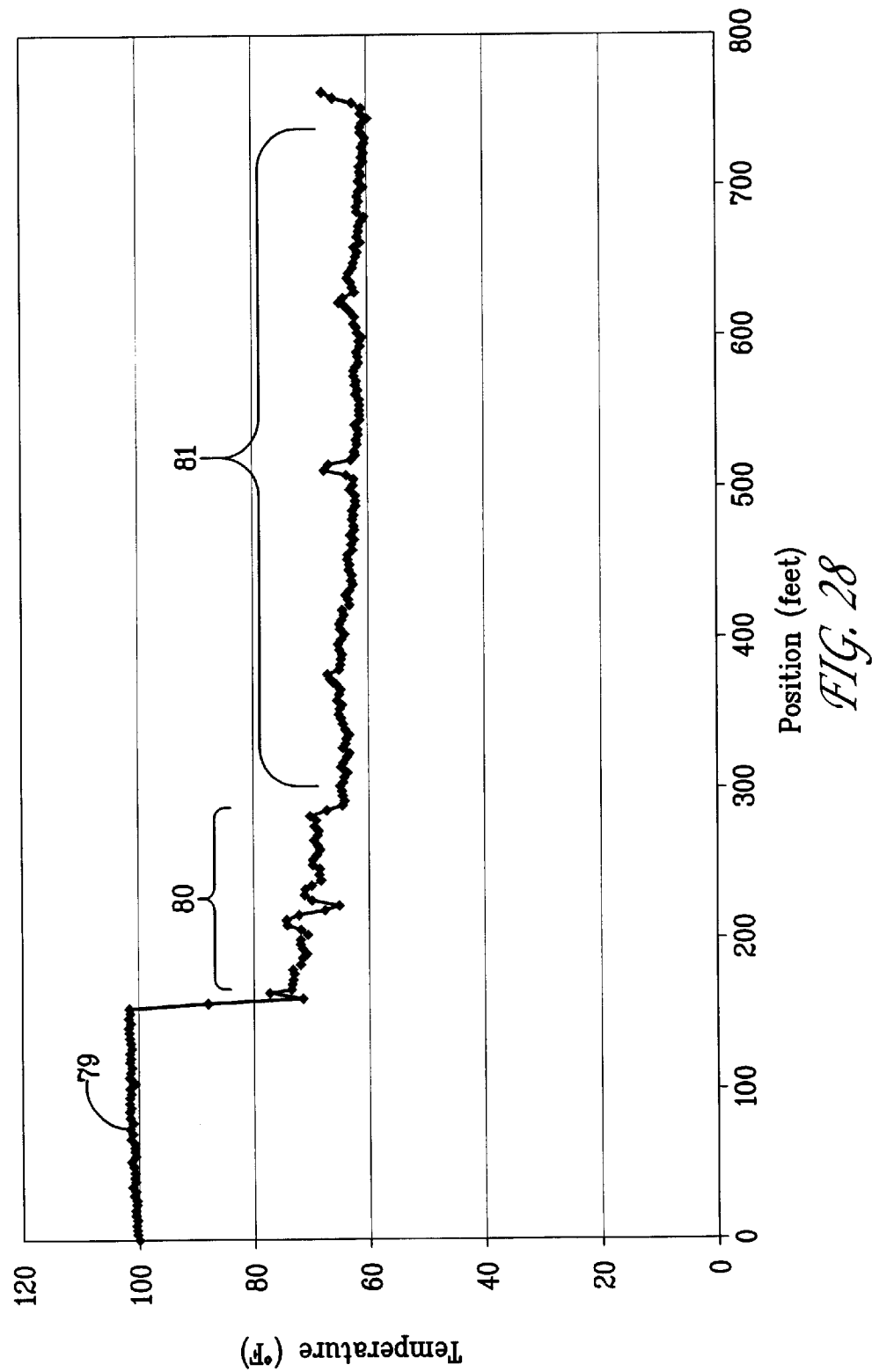

FIG. 28 shows a temperature profile along the fiber before any heat was applied. We note the uniform temperature 79 of the reference coil, the gradual reduction in temperature 80 along the lead fiber as it extends from the relatively warm instrument van to the start of the tubing. The tubing enters the ground at about the 295-foot point and emerges at about the 745-foot point. At about the 515-foot point is the short loop mentioned earlier. Apparently, the air temperature of about 65 F was higher than the typical underground temperature 81. The spatial variations in temperature are not due to noise in the DTS system; they are real. The constancy of the DTS reference-coil temperature is evidence that when the temperature is held constant, the DTS so indicates. In addition, in a separate test, a coil of fiber was immersed in a water bath at constant temperature and the DTS system also indicated a constant temperature. Furthermore, these variations are not surprising in view of the uncontrolled nature of the soil.

Figure 29:
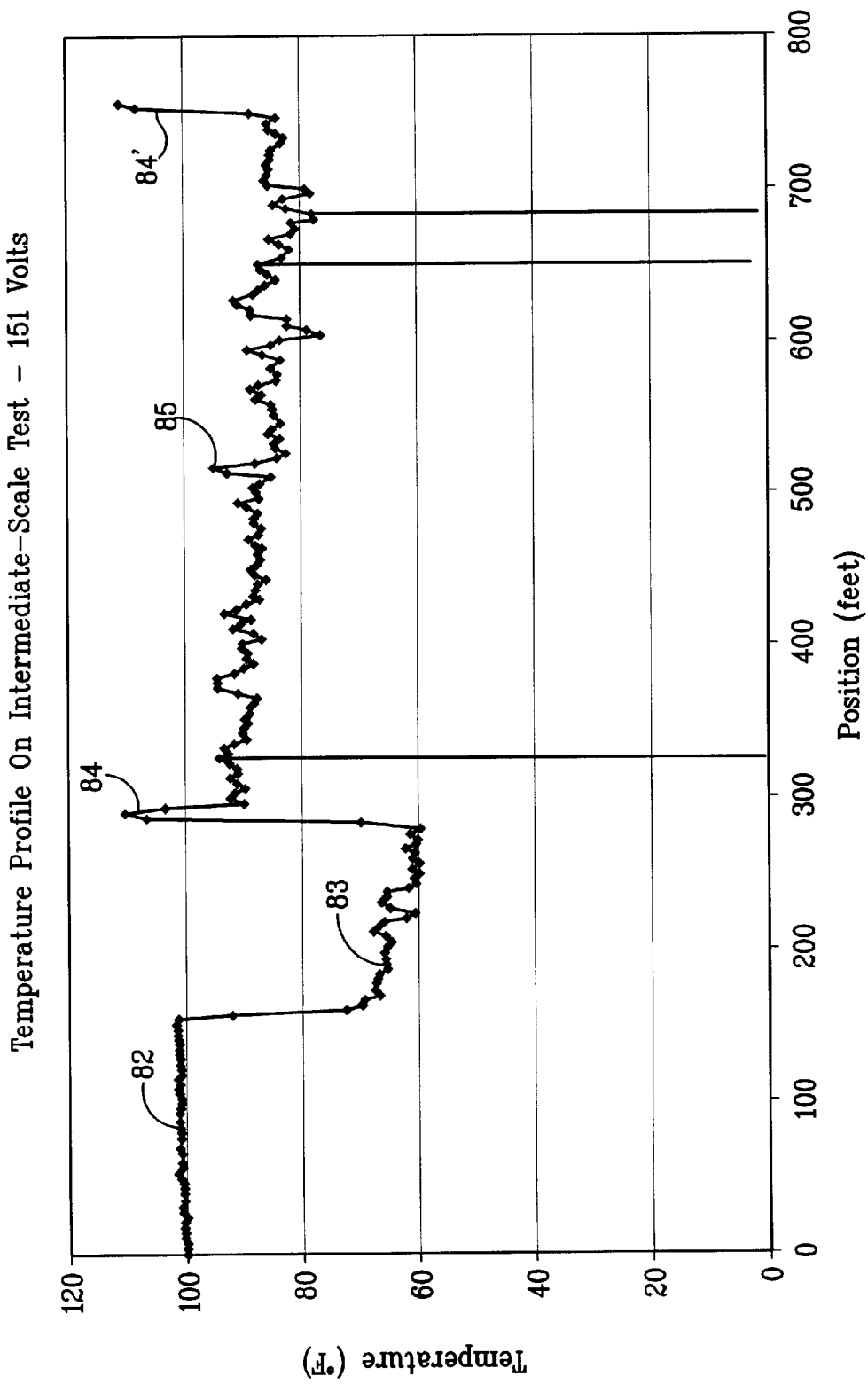
Figure 30:
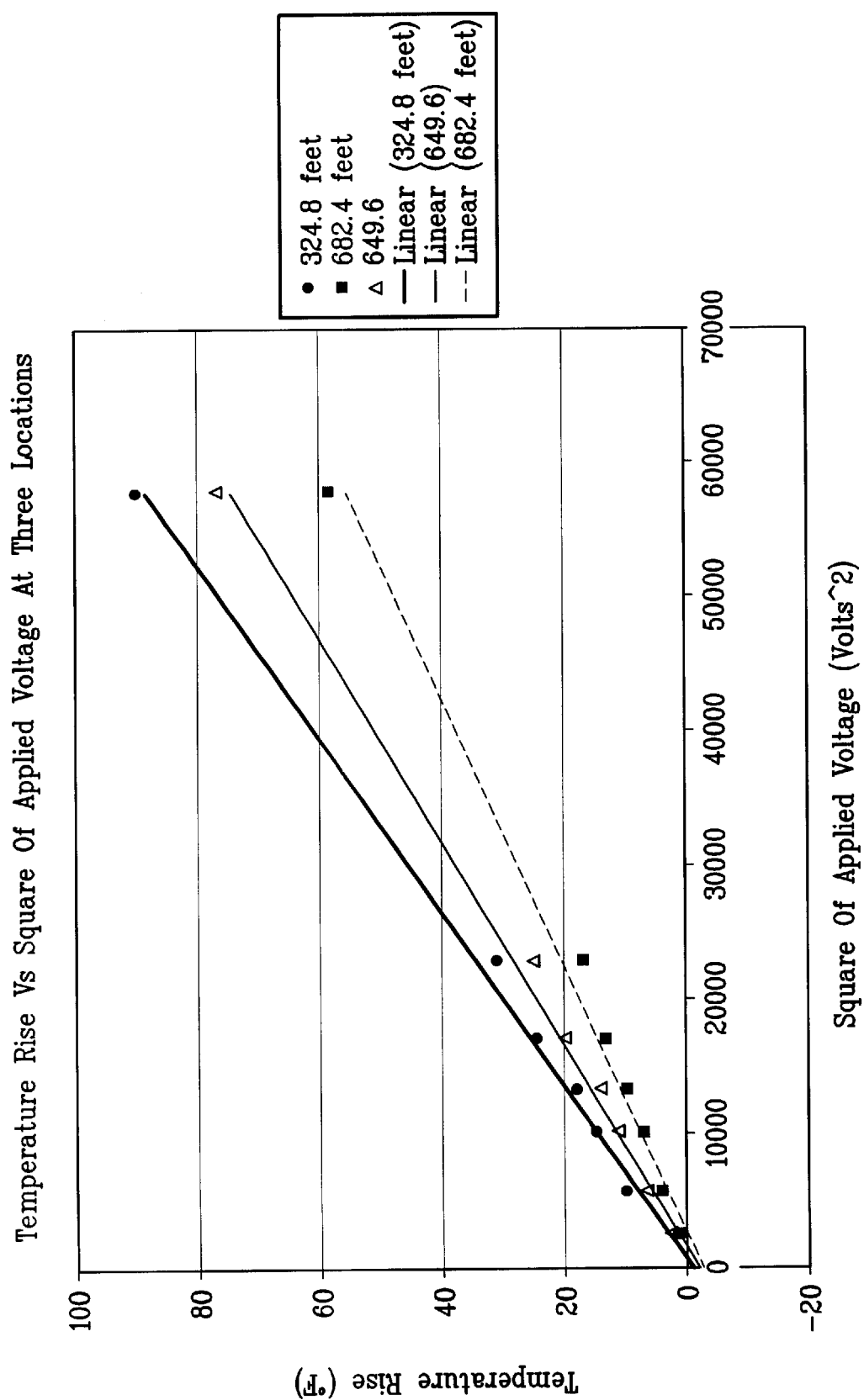

Voltage was then applied in stages to determine the relationship between an anticipated steady-state temperature and electrical power. For a simple system, whose components are unchanging, one expects a linear relationship between the two. The voltages applied were: 25, 50, 75, 100, 115, 130, 151, and 240 volts. The input power is, of course, proportional to the square of these values. FIG. 29 shows the steady-state temperature profile with 151 volts applied. We note the constant reference coil 82, the lead-in 83, and three hot spots. These are the sections of the tubing at either end 84, 84' and in the middle 85 that are in the air. Because they are not in contact with a large thermal mass, they are hotter than the fiber underground. In addition, we observe the complex temperature variation along the rest of the fiber. This behavior is not chaotic, however. FIG. 30 shows that the relationship between temperature rise and power at three points along the fiber (as indicated in FIG. 29) is, indeed, linear. [The electrical resistance of the tubing was, incidentally, about 0.045 ohms/foot] Thus, locally, the system is well behaved but depends in detail on the moisture content of the soil at a particular point. The figure also demonstrates that a considerable temperature rise is achievable using the tubing as a heater.

Figure 31:
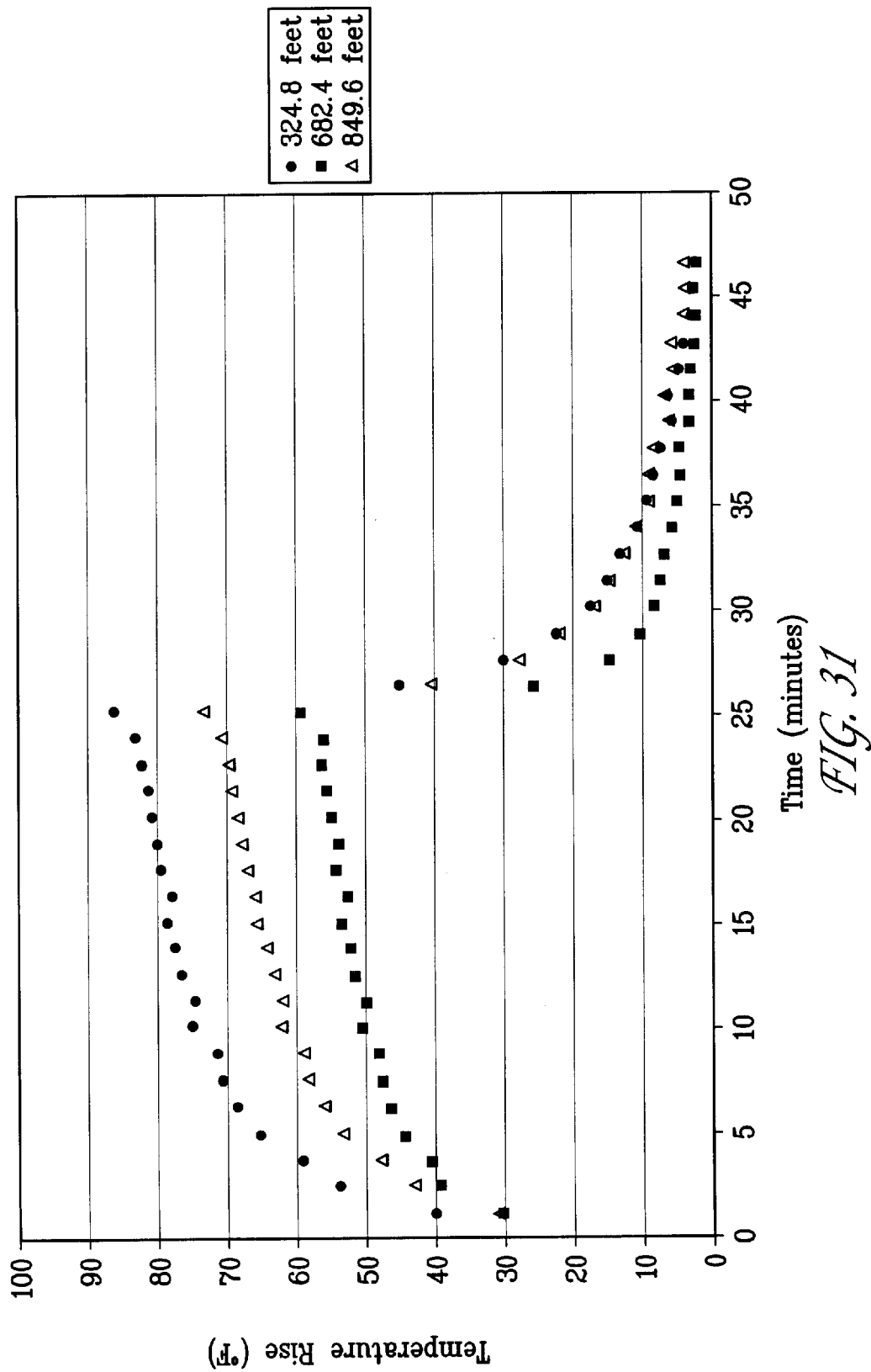

FIG. 31 also shows that although the data collected is complex, they are interpretable and represent an ordered system. The system was allowed to cool nearly completely after 151 volts was applied. Then, 240 volts was applied and DTS temperature measurements were obtained at the same three points during its rise to apparent steady state and subsequent cooling, after the voltage was removed. All three curves are qualitatively similar; each can probably be characterized by its own time constant and peak temperature. Both parameters should be useful in inferring moisture content from the data.

As a final point, the steady-state temperature discussed here can only be a pseudo-steady state because the heating will eventually cause a reduction in moisture content. Thus a true steady state is only achievable after all the moisture has disappeared. However, such a state would yield no information of any value. The pseudo-steady state is both useful and long-lived.

The invention being thus described, it will be obvious that the same may be varied in many ways. Such variations are not to be regarded as a departure from the spirit and scope of the invention, and all such modifications as would be obvious to one skilled in the art are intended to be included within the scope of the appended claims. It is intended that the scope of the invention be defined by the claims appended hereto. The entire disclosures of all references, applications, patents and publications cited above are hereby incorporated by reference.

I claim:

1. A soil moisture sensing system comprising:

a linear element positioned in a volume of soil, said linear element having a thickness and a length, said linear element comprising a distributed temperature sensing element coextensive with at least a portion of the length of said linear element, said distributed temperature sensing element being adapted to register changes in temperature of said soil including changes apparent following alteration of thermal conductance of said soil; and a heater which, when actuated, causes an increase in temperature of at least a portion of said soil, which increase is detectable by at least part of said distributed temperature sensing element.

2. The soil moisture sensing system of claim 1 wherein said linear element is arranged in a serpentine fashion within said volume of soil.

3. The soil moisture sensing system of claim 2 wherein said linear element passes through three dimensions within said volume of soil thereby distributing temperature sensing capability across a given target area and depth of said soil.

4. The soil moisture sensing system of claim 3 wherein said distributed temperature sensing element comprises an optical fiber through which pulses of radiation can travel generating Raman scattered radiation of different wavelengths and having different temperature dependencies.

5. The soil moisture sensing system of claim 4 wherein said heater comprises an element that is coextensive with at least a portion of said linear element.

6. The soil moisture sensing system of claim 5 wherein said heater is an electrical resistance heater.

7. The soil moisture sensing system of claim 6 wherein said heater comprises an element selected from the group consisting of a wire and a conduit enclosing said optical fiber.

8. A method for detecting moisture intrusion in soil comprising the steps of:

positioning in soil a linear element having a thickness and a length, said length being of a dimension greater than that of said thickness, said linear element comprising a distributed temperature sensing element coextensive with at least a portion of the length of said linear element, heating at least a portion of said soil, and measuring temperatures within said volume of soil, using said distributed temperature sensing element, to determine if temperature differences are apparent indicating presence of regions within said volume possibly having differing thermal conductance characteristics which respond differently to said heating.

9. The method of claim 8 wherein said step of measuring comprises:

transmitting at least one pulse of radiation through an optical fiber having a length, said optical fiber being coextensive with at least a portion of said linear element, whereby Raman scattered radiation is generated along the length of said optical fiber, said Raman scattered radiation comprising at least two separate wavelengths exhibiting different temperature dependencies, and comparing signals detected from the at least two separate wavelengths to determine temperature at a plurality of locations from which said Raman scattered radiation is generated along the length of said optical fiber.

10. The method of claim 9 wherein said heater comprises an element that is coextensive with at least a portion of said linear element.

11. The method of claim 10 wherein said heater is an electrical resistance heater.

12. The method of claim 11 wherein said heater comprises an element selected from the group consisting of a wire and a conduit enclosing said optical fiber.

13. A method of soil characterization comprising the steps of:

identifying at least one region within a volume of said soil, which has a lower temperature than at least one other region within said volume of said soil; and defining said at least one region having a lower temperature as having potentially greater concentration of moisture as compared with other regions.

14. The method according to claim 13 further comprising applying heat to at least a portion of said volume of said soil prior to said identifying step.

15. The method of claim 14 further comprising the step of positioning within said volume of said soil a distributed temperature sensing element according to a serpentine arrangement.

* * * * *